(12) United States Patent
Scharschmidt et al.

(10) Patent No.: US 9,561,197 B2
(45) Date of Patent: *Feb. 7, 2017

(54) METHODS OF THERAPEUTIC MONITORING OF PHENYLACETIC ACID PRODRUGS

(75) Inventors: Bruce Scharschmidt, San Francisco, CA (US); Masoud Mokhtarani, Walnut Creek, CA (US)

(73) Assignee: Horizon Therapeutics, LLC, Lake Forest, IL (US)

( * ) Notice: Subject to any disclaimer, the term of this patent is extended or adjusted under 35 U.S.C. 154(b) by 649 days.

This patent is subject to a terminal disclaimer.

(21) Appl. No.: 13/610,580

(22) Filed: Sep. 11, 2012

(65) Prior Publication Data

US 2013/0281530 A1    Oct. 24, 2013

Related U.S. Application Data

(60) Provisional application No. 61/636,256, filed on Apr. 20, 2012.

(51) Int. Cl.
| | | |
|---|---|---|
| A61K 31/192 | (2006.01) | |
| A61K 31/216 | (2006.01) | |
| A61K 31/225 | (2006.01) | |
| G01N 33/68 | (2006.01) | |

(52) U.S. Cl.
CPC ........... *A61K 31/192* (2013.01); *A61K 31/216* (2013.01); *G01N 33/6812* (2013.01)

(58) Field of Classification Search
CPC .............................. A61K 31/192; A61K 31/216
See application file for complete search history.

(56) References Cited

U.S. PATENT DOCUMENTS

| | | |
|---|---|---|
| 4,284,647 A | 8/1981 | Brusilow |
| 4,457,942 A | 7/1984 | Brusilow |
| 5,654,333 A | 8/1997 | Samid |
| 5,968,979 A | 10/1999 | Brusilow |
| 6,060,510 A | 5/2000 | Brusilow |
| 6,083,984 A | 7/2000 | Brusilow |
| 6,219,567 B1 | 4/2001 | Eggers |
| 8,094,521 B2 | 1/2012 | Levy |
| 8,404,215 B1 | 3/2013 | Scharschmidt et al. |
| 8,642,012 B2 | 2/2014 | Scharschmidt |
| 2003/0195255 A1 | 10/2003 | Summar |
| 2004/0229948 A1 | 11/2004 | Summar |
| 2005/0273359 A1 | 12/2005 | Young |
| 2006/0135612 A1 | 6/2006 | Ferrante |
| 2008/0119554 A1 | 5/2008 | Jalan |
| 2010/0008859 A1 | 1/2010 | Scharschmidt |
| 2010/0016207 A1 | 1/2010 | Wurtman et al. |
| 2012/0022157 A1 | 1/2012 | Scharschmidt |
| 2012/0220661 A1 | 8/2012 | Lee |
| 2013/0210914 A1 | 8/2013 | Scharschmidt |
| 2014/0142186 A1 | 5/2014 | Scharschmidt et al. |

FOREIGN PATENT DOCUMENTS

| | | |
|---|---|---|
| WO | WO94/22494 | 10/1994 |
| WO | WO 2005/053607 | 6/2005 |
| WO | WO 2006/056794 | 6/2006 |
| WO | WO 2007/005633 | 1/2007 |
| WO | WO 2009/087474 | 7/2009 |
| WO | WO 2009/134460 | 11/2009 |
| WO | WO 2010/025303 | 3/2010 |
| WO | WO 2012/028620 | 3/2012 |
| WO | WO2013/048558 | 4/2013 |
| WO | WO2013/158145 | 10/2013 |

OTHER PUBLICATIONS

Ambrose, A.M., (1933) "Further Studies on the Detoxification of Phyenylacetic Acid." *J Biol Chem* 101:669-675.
Batshaw M.L. et al. (Dec. 1980) "Treatment of Hyperammonemic Coma Caused by Inborn Errors of Urea Synthesis," *J Pediatr* 97(6):893-900.
Batshaw M.L. et al. (Jun. 10, 1982) "Treatment of Inborn Errors of Urea Synthesis: Activation of Alternative Pathways of Waste Nitrogen Synthesis and Excretion," *N. Engl J Med* 306(23):1387-1392.
Batshaw, M.L. (1984) "Hyperammonemia," in Current Problems in Pediatrics, Lockhart, J.D. ed.: Year Book Medical Publishers, pp. 2-69.
Batshaw, M.L. et al. (Aug. 1981) "New Approaches to the Diagnosis and Treatment of Inborn Errors of Urea Synthesis," *Pediatrics* 68(2):290-297.
Berry, G.T. et al., (2001) "Long-term Management of Patients with Urea Cycle Disorders." *J Pediatrics* 138:S56-S61.
Brahe, C., et al., (2005) "Phenylbutyrate Increases SMN Gene Expression in Spinal Muscular Atrophy Patients," *Eur J Hum Genet* 13:256-259.
Brunetti-Pierri, N., et al., (2011) "Phenylbutyrate Therapy for Maple Syrup Urine Disease," *Hum Mol Genet* 20(4):631-640.
Brusilow, S.W., et al. (Sep. 1, 1979) "New Pathways of Nitrogen Excretion in Inborn Errors of Urea Synthesis," *Lancet* 2(8140):452-454.
Brusilow, S.W., et al. (Feb. 8, 1980) "Amino Acid Acylation: A Mechanism of Nitrogen Excretion in Inborn Errors of Urea Synthesis," *Science* 207:659-661.
Brusilow, S.W., et al. (Jun. 21, 1984) "Treatment of Episodic Hyperammonemia in Children With Inborn Errors of Urea Synthesis," *N. Engl J Med* 310(25):1630-1634.
Brusilow, S.W., et al. (1991) Phenylacetylglutamine May Replace Urea as a Vehicle for Waste Nitrogen Excretion. *Pediatric Res* 29(2):147-150.
Brusilow, S.W., et al. (1991) "Treatment of Urea Cycle Disorders," Chapter 5 in Treatment of Genetic Diseases, Desnik, R.J. et al. eds, Churchill Livingstone, New York, New York, pp. 79-94.
Brusilow, S.W., et al. (1993) "Restoration of Nitrogen Homeostasis in a Man with Ornithine Transcarbamylase Deficiency." *J Metabolism* 42:1336-1339.
Brusilow, S.W., et al. (Jul. 25, 1994—Amendment Dated) "Protocols for Management of Intercurrent Hyperammonemia in Patients with Urea Cycle Disorders," FDA Application to Market a New Drug for Human Use or an Antibiotic Drug for Human Use, 14 pages.
Brusilow, S.W., et al. (1995) "Urea Cycle Disorders: Clinical Paradigm of Hyperammonemic Encephalopathy." *Prog Liver Diseases* 12:293-309.
Brusilow, S.W., et al. (1995) "Urea Cycle Enzymes," Chapter 32 in The Metabolic and Molecular bases of Inherited Diseases, Scriver, C.R. et al. eds., McGraw-Hill, Inc. New York, New York, pp. 1187-1232.

(Continued)

*Primary Examiner* — Jeffrey S Lundgren
*Assistant Examiner* — Sara E Townsley

(57) ABSTRACT

The present disclosure provides methods for adjusting the dosage of PAA prodrugs (e.g., HPN-100, PBA) based on measurement of PAA and PAGN in plasma and calculating the PAA:PAGN ratio so as to determine whether PAA to PAGN conversion is saturated.

2 Claims, 7 Drawing Sheets

(56) References Cited

OTHER PUBLICATIONS

Brusilow, S.W., et al. (1996) "Urea Cycle Disorders: Diagnosis, Pathophysiology, and Therapy," *Adv Pediatr* 43:127-170.
Calloway, D.H. et al. (1971) "Sweat and Miscellaneous Nitrogen Losses in Human Balance Studies," *J Nutrition* 101:775-786.
Calloway, D.H. et al. (1971) "Variation in Endogenous Nitrogen Excretion and Dietary Nitrogen Utilization as Determinants of Human Protein Requirements," *J Nutrition* 101:205-216.
Camacho, L.H. et al. "Phase I Dose Escalation Clinical Trial of Phenyl butyrate Sodium Administered Twice Daily to Patients With Advanced Solid Tumors," *Invest. New Drugs* 25:131-138 (2007, e-pub. Oct. 20, 2006).
Chang, J. et al., (2001) "Treatment of Spinal Muscular Atrophy by Sodium Butyrate," *PNAS* 98(17):9808-9813.
Chung, Y.L., et al., (2000) "A Novel Approach for Nasopharyngeal Carcinoma Treatment Uese Phenylbutyrate as a Protein Kinase C Modulator: Implications for Radiosensitization and EBV-Targeted Therapy," *Clin Cancer Res* 6:1452-1458.
ClinicalTrials.Gov/Archive View of NCT00551200 on Dec. 11, 2007 "Dose-Escalation Safety Study of Glyceryl Tri (4-Phenylbutyrate)(GT4P) to Treat Urea Cycle Disorders" [accessed Oct. 5, 2009], 4 pages.
Comte, B. et al., (2002) "Identification of Phenylbutyrylglutamine, a new Metabolite of Phenylbutyrate Metabolism in Humans," *J Mass Spectrometry*, 37(6):581-590.
Cudkowicz, ALS (2009) "Phase 2 Study of Sodium Phenylbutyrate in ALS," *Amyotrophic Lateral Sclerosis* 10:99-106.
Deferrari, G. et al. (1981) "Brain Metabolism of Amino Acids and Ammonia in Patients with Chronic Renal Insufficiency," *Kidney International* 20:505-510.
Diaz, G.A., et al., (2011) "Phase 3 Blinded, Randomized, Crossover Comparison of Sodium Phenylbutyrate (NaPBA) and Glycerol Phenylbutyrate (GPB): Ammonia (NH3) Control in Adults with Urea Cycle Disorders (UCDs)," *Mol. Genet. Metab.* 102:276.
Diaz, G.A.. et al.. "Phase 3 Blinded. Randomized, Crossover Comparison of Sodium Phenylbutyrate (NaPBA) and Glycerol Phenylbutyrate (GPB): Ammonia (NH3) Control in Adults with Urea Cycle Disorders (UCDs)," *Mol. Genet. Metab.* 102:276, *Society of Inherited Metabolic Disease* (SMID) Abstract.
Enns, G.M., et al., (2007) "Survival After Treatment with Phenylacetate and Benzoate for Urea-Cycle Disorders," *N. Eng J Med* 356:2282-2292.
FDA Label for Buphenyl, 6 pages.
FDA. "Buphenyl® (Sodium Phenylbutyrate) Label" nine pages (Aug. 2003).
Gargosky, S. (Aug. 2, 2005) "Improved Survival of Neonates Following Administration of Ammonul® (Sodium Phenyl acetate & Sodium Benzoate) 10% I 10% Injection," SSIEM Poster, six pages.
Gargosky, S. et al. (Oct. 14, 2005) "Results of a Twenty-two Year Clinical Trial: Actue, Adjunctive Pharmacological Treatment of Hyperammonemic Episodes in Patients with Deficiencies in Enzymes of the Urea Cycle," poster, Ucyclyd Pharma, Inc., one page.
Gargosky, S. (2006) "High Ammonia Levels Are Associated With Increased Mortality and Coma," Ucyclyd Pharma, Inc., one page.
Ghabril, M., et al., (2012) "Glycerol Phenylbutyrate (GPB) Administration in Patients with Cirrhosis and Episodic Hepatic Encephalopathy (HE)," accepted for presentation at Digestive Disease Week.
Gropman, A.L., et al., (2008) "1H MRS Allows Brain Phenotype Differentiation in Sisters with Late Onset Ornithine Transcarbamylase Deficiency (OTCD) and Discordant Clinical Presentations," *Mol Genet Metab* 94(1):52-60.
Gropman, A.L. et al. (2008) "1H MRS Identifies Symptomatic and Asymptomatic Subjects With Partial Ornithine Transcarbamylase Deficiency," *Mol Genet Metab* 95(1-2):21-30 (Sep.-Oct. 2008, e-pub. Jul. 26, 2008).
Gropman, A. (2010) "Brain Imaging in Urea Cycle Disorders," *Mol Genet Metab* 100:S20-S30.

Hines, P., et al., (2008) "Pulsed-Dosing with Oral Sodium Phenylbutyrate Increases Hemoglobin F in a Patient with Sickle Cell Anemia," *Pediatr Blood Cancer* 50:357-359.
Hogarth, P., et al., (2007) "Sodium Phenylbutyrate in Huntington's Disease: A Dose-Finding Study," *Mov Disord* 22(13):1962-1964.
Huang, H.H., et al., (2012) "Cannabinoid Receptor 2 Agonist Ameliorates Mesenteric Angiogenesis and Portosystemic Collaterals in Cirrhotic Rats," *Hepatology* 56:248-258.
Hyperion Therapeutics (Oct. 23, 2007) "Hyperion Therapeutics Announces Enrollment of First Patient in Phase 1/2 Clinical Trial of GT4P in Patients with Urea Cycle Disorders" Announcement, 1 page.
Hyperion Therapeutics. "Hyperion Therapeutics Announces Results for Phase II Study in Urea Cycle Disorders," located at <http://www.hyperiontx.com/press/release/pr1238518388,> last visited on Apr. 27, 2011, three pages (Mar. 30, 2009).
Hyperion Therapeutics. "Hyperion Therapeutics Announces Results of Phase I Study in Patients with Liver Cirrhosis" located at <http://www.hyperiontx.com/press/release/pr 1243891161>, last visited on Apr. 27, 2011, three pages (Jun. 2, 2009).
James, M.O. et al. (1972) "The Conjugation of Phenylacetic Acid in Man, Sub-Human Primates and Some Other Non-Primates Species," *Proc R Soc London* 182:25-35.
John, B.A. et al. (Mar. 2009) "The Disposition of HPN-100, a Novel Pharmaceutical Under Development for Potential Treatment of Hyperammonemia, in Cynomolgus Monkeys," ACMG 2009 ADME, poster, two pages.
John, B.A. et al. (Mar. 2009) "The Disposition of HPN-100, a Novel Pharmaceutical Under Development for Potential Treatment of Hyperammonemia, in Cynomologus Monkeys," abstract presented at ACMG 2009, one page.
Kasumov, T. et al., (2004) "New Secondary Metabolites of Phenylbutyrate in Humans and Rats," *Drug Metabolism and Disposition* 32(1):10-19.
Lee, B. et al. (2008) "Preliminary data on adult patients with urea cycle disorders (UCD) in an open-label, switch-over dose-escalation study comparing a new ammonia scavenger, glyceryl tri(4-phenylbutyrate) (HPN-100), to buphenyl (sodium phenylbutyrate (PBA))." *J Inherited Metabolic Disease* 31(1):91.
Lee, B. et al. (2009) "Dosing and Therapeutic Monitoring of Ammona Scavenging Drugs and Urinary Phenylacetylglutamine (PAGN) as a Biomarker: Lessons From a Phase 2 Comparison of a Novel Ammonia Scavenging Agent with Sodium Phenylbutyrate (NAPBA)," presented at ICIEM 2009, San Diego, CA, poster, one page.
Lee, B. et al. (2009) "Dosing and Therapeutic Monitoring of Ammonia Scavenging Drugs and Urinary Phenylacetylglutamine (PAGN) as a Biomarker; Lessons From a Phase 2 Comparison of a Novel Ammonia Scavenging Agent With Sodium Phenylbutyrate (NaPBA)," abstract presented at ICIEM 2009, San Diego, CA, one page.
Lee, B. et al. (2009) "Phase 2 Study of a Novel Ammonia Scavenging Agent in Adults With Urea Cycle Disorders (UCDs)," abstract presented at ACMG 2009, one page.
Lee, B. et al. (2009) "Phase 2 Study of a Novel Ammonia Scavenging Agent in Adults with Urea Cycle Disorders (UCDs)," presented at ACMG 2009, seventeen pages.
Lee, B., et al. (2010) "Phase 2 Comparison of a Novel Ammonia Scavenging Agent with Sodium Phenylbutyrate in Patients with Urea Cycle Disorders: Safety, Pharmacokinetics and Ammonia Control," *Mol Genet Metab* 100:221-228.
Lewis, H.B. (1914) "Studies in the Synthesis of Hippuric Acid in the Animal Organism. II. The Synthesis and Rate of Elimination of Hippuric Acid After Benzoate Ingestion in Man," *J Biol Chem* 18:225-231.
Liang, K.Y., et al., (1986) "Longitudinal Data Analysis Using Generalized Linear Models," *Biometrika* 73(1):13-22.
Lichter-Konecki, U., et al., "Ammonia Control in Children with Urea Cycle Disorders (UCDs); Phase 2 Comparison of Sodium Phenyl butyrate and Glycerol Phenylbutyrate," *Mol Genet Metab* 103:323-329 (2011).
MacArthur, R. B., et al., "Pharmacokinetics of sodium phenylacetate and soium benzoate following intravenous

(56) References Cited

OTHER PUBLICATIONS administrtion as both a bolus and continuous infusion to healthy adult volunteers." *Mol Genet Metab* 81:(1):S67-S73 (2004).
Maestri, N. E. et al. "Plasma Glutamine Concentration: A Guide in the Management of Urea Cycle Disorders," *J Pediatr* 121(2):259-261(Aug. 1992).
Mansour, A. et al. "Abdominal Operations in Patients with Cirrhosis: Still a Major Surgical Challenge," *Surgery* 122(4):730-735. (Abstract Only.) (Oct. 1997).
McGuire, B. et al. (2008) "Pharmacokinetic (PK) Safety Study of Sodium Phenylacetate and Sodium Benzoate Administered to Subjects with Hepatic Impairment," abstract of The 13th International Symposium, Abano (Padova), Italy, Apr. 28-May 1, 2008, two pages.
McGuire, B. et al. (2008) Pharmacokinetic Safety Study of Sodium Phenylacetate and Sodium Benzoate Administered to Subjects With Hepatic Impairments, *Liver International* 28:743. (Abstract Only).
McGuire, B. et al. (2009) "Pharmacokinetic (PK) and Safety Analyses of a Novel Ammonia-Reducing Agent in Healthy Adults and Patients with Cirrhosis," Hyperion Therapeutics, poster, one page.
McGuire, B. et al. (2009) "Pharmacokinetic (PK) and Safety Analyses of a Novel Ammonia-Reducing Agent in Healthy Adults and Patients with Cirrhosis," abstract presented at DDW, two pages.
McGuire, B. et al., (2010) "Pharmacology and Safety of Glycerol Phenylbutyrate in Healthy Adults and Adults with Cirrhosis," *Hepatology* 51:2077-2085.
McQuade P.S. (1984) "Analysis and the Effects of Some Drugs on the Metabolism of Phenylethylamine and Phenylacetic Acid," *Neuropsychopharmaco Biol Psychiat* 8:607-614.
Mercuri, E., et al., (2004) "Pilot Trial of Phenylbutyrate in Spinal Muscular Atrophy," *Neuromuscul Disord* 14:130-135.
Mokhtarani, M., et al., (2012) "Elevated Phenylacetic Acid (PAA) Levels Appear Linked to Neurological Adverse Events in Healthy Adults But Not in Urea Cycle Disorder (UCD) Patients," *Mol Genet Metab* 105:342.
Moldave, K., et al., (1957) "Synthesis of Phenylacetylglutamine by Human Tissue," *J Biol Chem* 229:463-476.
Monteleone, JPR, et al., (2012) "Population pk Analysis of Glycerol Phenylbutyrate (GPB) and Sodium Phenylbutyrate(NAPBA) in Adult and Pediatric Patients with Urea Cycle Disorders," *Mol Genet Metab* 105:343.
Ong, J. P., et al., (2003) "Correlation Between Ammonia Levels and the Severity of Hepatic Encephalopathy," *Am J Med* 114:188-193.
Perrine, S. P., (2008) "Fetal Globin Stimulant Therapies in the Beta-Hemoglobinopathies: Principles and Current Potential," *Pediatr Ann* 37(5):339-346.
Piscitelli, S.C. et al. (1995) "Disposition of Phenylbutyrate and its Metabolites, Phenylacetete and Phenylacetylglutamine," *J Clin Pharmacal* 35:368-373.
Propst, A. et al. (1995) "Prognosis and Life Expectancy in Chronic Liver Disease," *Dig Dis Sci* 40(8):1805-1815. (Abstract Only).
Riley, T.R. et al. (2001) "Preventive Strategies in Chronic Liver Disease: Part II. Cirrhoses," *Am Fam Physician* 64(10):1735-1740. (Abstract Only).
Rudman, D., et al., (1973) "Maximal Rates of Excretion and Synthesis of Urea in Normal and Cirrhotic Subjects," *J Clin Invest* 52:2241-2249.
Ryu, H., et al., (2005) "Sodium Phenylbutyrate Prolongs Survival and Regulates Expression of Anti-Apoptotic Genes in Transgenic Amyotrophic Lateral Sclerosis Mice," *J Neurochem* 93:1087-1098.
Shiple, G.J. et al. (1922) "Synthesis of Amino Acids in Animal Organisms. I. Synthesis of Glycocoll and Glutamine in the Human Organism," *J Am Chem Soc* 44:618-624.
Simell, O., et al. (1986) "Waste nitrogen excretion via amino acid acylation: Benzoate and phyylacetate in lysinuric protein intolerance." *Ped Res* 20(11):1117-1121.
Singh, (2001) "Consensus Statement from a Conference for the Management of Patients with Urea Cycle Disorders," *Suppl to J Pediatrics* 138(1):S1-S5.

Stauch, et al., (1998) "Oral L-ornithine-L-aspartate therapy of chronic hepatic encephalopathy: results of a placebo-controlled double-blind study" *J Hepatology* 28(5):856-864.
Summar, M. et al. (2007) "Description and Outcomes of 316 Urea Cycle Patients From a 21-Year, Multicenter Study of Acute Hyperammonemic Episodes," Abstract, presented at Annual Symposium CCH—Congress Centre Hamburg, Sep. 4-7, 2007, GSSIEM 2007, two pages.
Summar, M.L. et al. "Diagnosis, Symptoms, Frequency and Mortality of 260 Patients with Urea Cycle Disorders From a 21-Year, Multicentre Study of Acute Hyperammonaemic Episodes," *Acta Paediatr* 97:1420-1425 (Oct. 2008, e-pub. Jul. 17, 2008).
Swedish Orphan International, "Urea Cycle Disorders an International Perspective," Poster, Symposium Swedish Orphan International, Barcelona, Spain, Jan. 12, 2007, one page.
Tanner, L. M., et al., (2007) "Nutrient intake in lysinuric protein intolerance." *J Inherited Metabolic Disease* 30(5):716-721.
Thibault, A. et al., (1994) "A Phase I and Pharmacokinetic Study of Intravenous Phenylacetate in Patients with Cancer," *Cancer Res* 54(7):1690-1694.
Thibault, A., et al., (1995) "Phase I Study of Phenylacetate Administered Twice Daily to Patients with Cancer," *Cancer* 75(12):2932-2938.
Tuchman, M. et al. (2008) "Cross-Sectional Multicenter Study of Patients With Urea Cycle Disorders in the United States," *Malec Genetics Metab* 94:397-402 (e-pub. Jun. 17, 2008).
Waterlow, J.C. (1963) "The Partition of Nitrogen in the Urine of Malnourished Jamaican Infants," *Am J Clin Nutrition* 12:235-240.
Xie, G., et al., (2012) "Role of Differentiation of Liver Sinusoidal Endothelial Cells in Progression and Regression of Hepatic Fibrosis in Rats," *Gastroenterology* 142:S918.
Zeitlin, P.L. et al. (2002) "Evidence of CFTR Function in Cystic Fibrosis After System Administration of 4-Phenylbutyrate," *Mol Therapy* 6(1):119-126.
Combined Search and Examination Report for British Patent Application No. GB0915545.8, search completed Oct. 8, 2009, report dated Oct. 9, 2009.
Combined Search and Examination Report for British Patent Application No. GB1013468.2, search completed Sep. 8, 2010, report dated Sep. 9, 2010.
European Patent Office, Extended European Search Report for EP09739263 completed Nov. 2, 2011.
European Patent Office, International Search Report and Written Opinion for PCT/US2009/055256 completed Dec. 18, 2009 and mailed Dec. 30, 2009.
Examination Report for British Patent Application No. GB0915545.8 dated Feb. 5, 2010.
Examination Report for British Patent Application No. GB0915545.8 dated May 11, 2010.
Examination Report for British Patent Application No. GB0915545.8 dated Oct. 27, 2010.
Examination Report for British Patent Application No. GB1013468.2 dated Oct. 28, 2011.
International Preliminary Report on Patentability (Ch I) for PCT/US2012/028620, completed Jun. 4, 2012 and mailed on Apr. 10, 2014.
International Preliminary Report on Patentability (Ch II) for PCT/US2012/028620, completed Aug. 22, 2013 and mailed Sep. 4, 2013.
International Preliminary Report on Patentability for PCT/US2009/030362, completed Feb. 24, 2009 and mailed on Mar. 10, 2011.
International Preliminary Report on Patentability for PCT/US2009/055256, completed on Aug. 27, 2009, mailed on Mar. 10, 2011.
United States Patent and Trademark Office, International Search Report and Written Opinion for PCT/US2009/030362 mailed Mar. 2, 2009.
United States Patent and Trademark Office, International Search Report and Written Opinion for PCT/US2012/028620 mailed Jun. 20, 2012.
United States Patent and Trademark Office, International Search Report and Written Opinion for PCT/US2012/54673 mailed Nov. 20, 2012.

(56) References Cited

OTHER PUBLICATIONS

United States Patent and Trademark Office, International Search Report and Written Opinion for PCT/US2013/71333 mailed Mar. 28, 2014.
Amodio, P., et al., "Detection of Minimal Hepatic Encephalopathy: Normalization and Optimization of the Psychometric Hepatic Encephalopathy Score. A Neuropsychological and Quantified EEG Study," J. Hepatol. 49:346-353 (2008).
ANDA Notice Letter, Par Pharmaceutical, Inc. to Hyperion Therapeutics, inc.. Re: Glycerol Phenylbutyrate 1.1 gm/ml oral liquid; U.S. Pat. Nos. 8,404,215 and 8,642,012 Notice of Paragraph IV Certification Mar. 12, 2014.
Bajaj, J. S., et al., "Review Article: The Design of Clinical Trials in Hepatic Encephalopathy—An International Society for Hepatic Encephalopathy and Nitrogen Metabolism (ISHEN) Consensus Statement," Aliment Pharmacol Ther. 33 (7):739-747 (2011).
Barsotti, Measurement of Ammonia in Blood, 138 J. Pediatrics, S11-S20 (2001).
Batshaw, et al., Treatment of Carbamyl Phosphate Synthetase Deficiency with Keto Analogues of Essential Amino Acids, 292 The New England J. Medicine, 1085□90 (1975).
Batshaw, M. L. et. al., Alternative Pathway Therapy for Urea Cycle Disorder: Twenty Years Later, 138 J. Pediatrics S46 (2001).
Blau, Duran, Blaskovics, Gibson (editors), Physician's Guide to the Laboratory Diagnosis of Metabolic Diseases, 261-276 (2d ed. 1996).
Blei, A. T., et al., "Hepatic Encephalopathy," Am. J. Gastroenterol. 96(7):1968-1976 (2001 ).
Burlina, A.B. et al., Long-Term Treatment with Sodium Phenylbutyrate in Ornithine Transcarbamylase-Deficient Patients, 72 Molecular Genetics and Metabolism 351-355 (2001).
Carducci, M., Phenylbutyrate Induces Apoptosis in Human Prostate Cancer and Is More Potent Than Phenylacetate, 2 Clinical Cancer Research 379 (1996).
Carducci, M.A. et al., A Phase I Clinical and Pharmacological Evaluation of Sodium Phenylbutyrate on an 120-h Infusion Schedule, 7 Clin. Cancer Res. 3047 (2001).
Center for Drug Evaluation and Research, Clinical Pharmacology and Biopharmaceutics Review for New Drug Application No. 20-645 (Ammonul®) (2005).
Center for Drug Evaluation and Research, Labeling for New Drug Application No. 20-645 (Ammonul®) (2005).
Center for Drug Evaluation and Research, Medical Review for New Drug Application No. 20-645 (Ammonul®) (2005).
Chen, Z. et al., Tributyrin: A Prodrug of Butyric Acid for Potential Clinical Application in Differentiation Therapy, 54 Cancer Research 3494 (1994).
Clay, A. et. al, Hyperammonemia in the ICU, 132 Chest 1368 (2007).
Collins, A.F. et al., Oral Sodium Phenylbutyrate Therapy in Homozygous Beta Thalassemia: A Clinical Trial, 85 Blood 43 (1995).
Conn, H. O., et al., "Liver Physiology and Disease: Comparison of Lactulose and Neomycin in the Treatment of Chronic Portal-Systemic Encephalopathy. A Double Blind Controlled Trial," Gastroenterology 72(4):573-583 (1977).
Cordoba, J., "New Assessment of Hepatic Encephalopathy," Journal of Hepatology 54: 1030-1040 (2011 ).
Darmaun, D. et al., Phenylbutyrate-Induced Glutamine Depletion in Humans: Effect on Leucine Metabolism, 5 Am. J. of Physiology: Endocrinology and Metabolism E801 (1998).
Diaz, G. A., et al., "Ammonia Control and Neurocognitive Outcome Among Urea Cycle Disorder Patients Treated with Glycerol Phenylbutyrate," Hepatology 57(6):2171-2179 (2013).
Dixon, M. A. and Leonard, J.V., Intercurrent Illness in Inborn Errors of Intermediary Metabolism, 67 Archives of Disease in Childhood 1387 (1992).
Dover, G. et al, Induction of Fetal Hemoglobin Production in Subjects with Sickle Cell Anemia by Oral Sodium Phenylbutyrate, 54 Cancer Research 3494 (1994).
Endo, F. et al., Clinical Manifestations of Inborn Errors of the Urea Cycle and Related Metabolic Disorders During Childhood, 134 J. Nutrition 1605S (2004).
European Medicines Agency, Annex I: Summary of Product Characteristics for Ammonaps.
European Medicines Agency, European Public Assessment Report: Summary for the Public for Ammonaps (2009).
European Medicines Agency, Scientific Discussion for Ammonaps (2005).
European Medicines Agency, Scientific Discussion for Carbaglu (2004).
FDA Label for Carbaglu, seven pages. (Mar. 2010).
Feillet, F. and Leonard, J.V., Alternative Pathway Therapy for Urea Cycle Disorders, 21 J. Inher. Metab. Dis. 101-111 (1998).
Feoli-Fonseca, M. L., Sodium Benzoate Therapy in Children with Inborn Errors of Urea Synthesis: Effect on Carnitine Metabolism and Ammonia Nitrogen Removal, 57 Biochemical and Molecular Medicine 31 (1996).
Ferenci, P., et al., "Hepatic Encephalopathy—Definition, Nomenclature, Diagnosis, and Quantification: Final Report of the Working Party at the 11th World Congresses of Gastroenterology, Vienna, 1998," Hepatology 35:716-721 (2002).
Fernandes, Saudubray, Berghe (editors), Inborn Metabolic Diseases Diagnosis and Treatment, 219-222 (3d ed. 2000).
Geraghty, M.T. and Brusilow, S.W., Disorders of the Urea Cycle, in Liver Disease in Children 827 (F.J. Suchy et al., eds. 2001).
Ghabril, M. et al., "Glycerol Phenylbutyrate in Patients with Cirrhosis and Episodic Hepatic Encephalopathy: A Pilot Study of Safety and Effect on Venous Ammonia Concentration," Clinical Pharmacology in Drug Development 2(3): 278-284 (2013).
Gilbert, J. et al., A Phase I Dose Escalation and Bioavailability Study of Oral Sodium Phenylbutyrate in Patients with Refractory Solid Tumor Malignancies, 7 Clin. Cancer Research 2292-2300 (2001).
Gore, S. et al., Impact of the Putative Differentiating Agent Sodium Phenylbutyrate on Myelodysplastic Syndromes and Acute Myeloid Leukemia, 7 Clin. Cancer Res. 2330 (2001).
Gropman, A.L. et al., Neurological Implications of Urea Cycle Disorders, 30 J. Inherit Metab Dis. 865 (2007).
Hassanein, T. I., et al., "Randomized Controlled Study of Extracorporeal Albumin Dialysis for Hepatic Encephalopathy in Advanced Cirrhosis," Hepatology 46:1853-1862 (2007).
Hassanein, T. I., et al., "Introduction to the Hepatic Encephalopathy Scoring Algorithm (HESA)," Dig. Dis. Sci. 53:529-538 (2008).
Hassanein, T., et al., "Performance of the Hepatic Encephalopathy Scoring Algorithm in a Clinical Trial of Patients With Cirrhosis and Severe Hepatic Encephalopathy," Am. J. Gastroenterol. 104:1392-1400 (2009).
Honda, S. et al., Successful Treatment of Severe Hyperammonemia Using Sodium Phenylacetate Power Prepared in Hospital Pharmacy, 25 Biol. Pharm. Bull. 1244 (2002).
International Search Report and Written Opinion for PCT/US09/30362, mailed Mar. 2, 2009, 8 pages.
International Search Report and Written Opinion for PCT/US2009/055256, mailed Dec. 30, 2009, 13 pages.
Inter Partes Review of U.S. Pat. No. 8,404,215 Petition Apr. 29, 2015.
Inter Partes Review of U.S. Pat. No. 8,642,012 Petition Apr. 29, 2015.
Kleppe, S. et al., Urea Cycle Disorders, 5 Current Treatment Options in Neurology 309-319 (2003).
Kubota, K. and Ishizaki, T., Dose-Dependent Pharmacokinetics of Benzoic Acid Following Oral Administration of Sodium Benzoate to Humans, 41 Eur. J. Clin. Pharmacol. 363 (1991).
Lee, B. and Goss, J., Long-Term Correction of Urea Cycle Disorders, 138 J. Pediatrics S62 (2001).
Lee, B. et al., Considerations in the Difficult-to-Manage Urea Cycle Disorder Patient, 21 Crit. Care Clin. S19 (2005).
Lee, B., et al., "Optimizing Ammonia (NH3) Control in Urea Cycle Disorder (UCD) Patients: A Predictive Model," Oral Abstract Platform Presentations, Biochemical Genetics, Phoenix, AZ, Mar. 22, 2013.

(56) References Cited

OTHER PUBLICATIONS

Leonard, J.V., Urea Cycle Disorders, 7 Semin. Nenatol. 27 (2002).
Lizardi-Cervera, J. et al., Hepatic Encephalopathy: A Review, 2 Annals of Hepatology 122-120 (2003).
Maestri NE, et al., Prospective treatment of urea cycle disorders. J Paediatr 1991;119:923-928.
Maestri, N.E., et al., Long-Term Survival of Patients with Argininosuccinate Synthetase Deficiency, 127 J. Pediatrics 929 (1995).
Maestri, N.E., Long-Term Treatment of Girls with Ornithine Transcarbamylase Deficiency, 355 N. Engl. J. Med. 855 (1996).
Majeed, K., Hyperammonemia, eMedicine.com (Dec. 2001).
Marini, J.C. et al., Phenylbutyrate Improves Nitrogen Disposal via an Alternative Pathway without Eliciting an Increase in Protein Breakdown and Catabolism in Control and Ornithine Transcarbamylase-Deficient Patients, 93 Am. J. Clin. Nutr. 1248 (2011).
Matsuda, I., Hyperammonemia in Pediatric Clinics: A Review of Ornithine Transcarbamylase Deficiency (OTCD) Based on our Case Studies, 47 JMAJ 160 (2004).
Mizutani, N. et al., Hyperargininemia: Clinical Course and Treatment with Sodium Benzoate and Phenylacetic Acid, 5 Brain and Development 555 (1983).
Mokhtarani, M., et al., (2013) "Elevated Phenylacetic Acid Levels Do Not Correlate with Adverse Events in Patients with Urea Cycle Disorders o rHepatic Encephalopathy and Can Be Predicted Based on the Plasma PAA to PAGN Ratio," Mol Genet Metab 110(4):446-453.
Mokhtarani, M., et al., (2012) "Urinary Phenylacetylglutamine as Dosing Biomarker for Patients with Urea Cycle Disorders," Mol Genet Metab 107(3):308-314.
Monteleone, JPR, et al., (2013) "Population Pharmacokinetic Modeling and Dosing Simulations of Nitrogen-Scavenging Compounds: Disposition of Glycerol Phenylbutyrate and Sodium Phenylbutyrate in Adult and Pediatric Patients with Urea Cycle Disorders," J. Clin. Pharmacol. 53(7): 699-710.
Munoz, S. J., "Hepatic Encephalopathy," Med. Clin. N. Am. 92:795-812 (2008).
Nassogne, M.C., Urea Cycle Defects: Management and Outcome, 28 J. Inherit. Metab. Dis. 407 (2005).
New England Consortium of Metabolic Programs, Acute Illness Protocol: Urea Cycle Disorders: The Infant/Child with Argininosuccinate Lyase Deficiency, adapted from Summar, M and Tuchman, M, Proceedings of a Consensus Conference for the Management of Patients with Urea Cycle Disorders, 138 J. Peds. Suppl. S6 (2001).
New England Consortium of Metabolic Programs, Acute Illness Protocol: Urea Cycle Disorders: The Infant/Child with Citrullinemia, adapted from Summar, M and Tuchman, M, Proceedings of a Consensus Conference for the Management of Patients with Urea Cycle Disorders, 138 J. Peds. Suppl. S6 (2001).
Newmark, H. L. and Young, W. C., Butyrate and Phenylacetate as Differentiating Agents: Practical Problems and Opportunities, 22 J. Cellular Biochemistry 247 (1995).
Ortiz, M., et al., "Development of a Clinical Hepatic Encephalopathy Staging Scale," Aliment Pharmacol Ther 26:859-867 (2007).
Par Pharmaceutical, Inc.'S Initial Invalidity Contentions and Non-Infringement Contentions for U.S. Pat. Nos. 8,404,215 and 8,642,012.
Parsons-Smith, B. G., et al., "The Electroencephalograph in Liver Disease," Lancet 273:867-871 (1957).
Phuphanich, S. et al., Oral Sodium Phenylbutyrate in Patients with Recurrent Malignant Gliomas: A Dose Escalation and Pharmacologic Study, Neuro-Oncology 177 (2005).
Praphanproj, V. et al., Three Cases of Intravenous Sodium Benzoate and Sodium Phenylacetate Toxicity Occurring in the Treatment of Acute Hyperammonemia, 23 J. Inherited Metabolic Disease 129 (2000).
Rockey, D. C., et al., "Randomized, Controlled, Double Blind Study of Glycerol Phenylbutyrate in Patients with Cirrhosis and Episodic Hepatic Encephalopathy," Hepatology 56:248(A) (2012).

Salam, M., et al., "Modified-Orientation Log to Assess Hepatic Encephalopathy," Aliment Pharmacol Ther. 35(8):913-920 (2012).
Scientific Discussion for Ammonaps, EMEA 2005, available at http://www.ema.europa.eu/docs/en_GB/document_library/EPAR___Scientific_Discussion/human/000219/WC500024748.pdf.
Scottish Medicines Consortium, Carglumic Acid 200 mg Dispersible Tablets (Carbaglu®) No. 299/06 (Sep. 8, 2006).
Seakins, J.W.T., The Determination of Urinary Phenylacetylglutamine as Phenylacetic Acid: Studies on its Origin in Normal Subjects and Children with Cystic Fibrosis, 35 Clin. Chim. Acta.121 (1971).
Sherwin, C. et al., The Maximum Production of Glutamine by the Human Body as Measured by the Output of Phenylacetylglutamine, 37 J. Biol. Chem. 113 (1919).
Smith, W., et al., "Ammonia Control in Children Ages 2 Months through 5 Years with Urea Cycle Disorders: Comparison of Sodium Phenylbutyrate and Glycerol Phenylbutyrate," J Pediatr. 162(6):1228-1234.e1 (2013).
Summar, M., Current Strategies for the Management of Neonatal Urea Cycle Disorders, 138 J. Pediatrics S30 (2001).
Summar, M. and Tuchman, M., Proceedings of a Consensus Conference for the Management of Patients with Urea Cycle Disorders, 138 J. Pediatrics S6 (2001).
Summar, M., Urea Cycle Disorders Overview, Gene Reviews, www.genetests.org (Apr. 2003).
Summar, M. et al., Unmasked Adult-Onset Urea Cycle Disorders in the Critical Care Setting, 21 Crit. Care Clin. S1 (2005).
The National Organization for Rare Disorders (2012). The Physician's Guide to Urea Cycle Disorders, at http://nordphysicianguides.org/wp-content/uploads/2012/02/NORD_Physician_Guide_to_Urea_Cycle_Disorders.pdf.
Todo, S. et al., Orthotopic Liver Transplantation for Urea Cycle Enzyme Deficiency, 15 Hepatology 419 (1992).
Tuchman, M., and Yudkoff, M., Blood Levels of Ammonia and Nitrogen Scavenging Amino Acids in Patients with Inherited Hyperammonemia, 66 Molecular Genetics and Metabolism 10-15 (1999).
United States Patent and Trademark Office, International Search Report and Written Opinion dated Jan. 16, 2015 for PCT/US14/58489.
United States Patent and Trademark Office, International Search Report and Written Opinion for PCT/US2014/060543 dated Jan. 23, 2015.
Vilstrup, H., et al., "Hepatic Encephalopathy in Chronic Liver Disease: 2014 Practice Guideline by the American Association for the Study of Liver Diseases and the European Association for the Study of the Liver," Hepatology 60 (2):715-735 (2014).
Walsh et al., Chemical Abstract vol. 112, No. 231744.
Welbourne, T. et al., The Effect of Glutamine Administration on Urinary Ammonium Excretion in Normal Subjects and Patients with Renal Disease, 51 J. Clin. Investigation 1852 (1972).
Wilcken, B., Problems in the Management of Urea Cycle Disorders, 81 Molecular Genetics and Metabolism 85 (2004).
Wilson, C.J., et al., Plasma Glutamine and Ammonia Concentrations in Ornithine Carbamoyltransferase Deficiency and Citrullinaemia, 24 J. Inherited Metabolic Disease 691 (2001).
Wright, G., et al., Management of Hepatic Encephalopathy, 2011 International Journal of Hepatology 1 (2011).
Wright, P., Review: Nitrogen Excretion: Three End Products, Many Physiological Roles, 198 J. Experimental Biology 273 (1995).
Yajima, et al. Diurnal Fluctuations of Blood Ammonia Levels in Adult-Type Citrullinemia, 137 Tokohu J. Ex/ Med, 213-220 (1982).
Yu, Ryan and Potter, Murray, Diagnosis of Urea Cycle Disorders in Adulthood: Late-Onset Carbamyl Phosphate Synthetase 1 Deficiency, 7 MUMJ 30 (2010).
Yudkoff, M. et al., In Vivo Nitrogen Metabolism in Ornithine Transcarbamylase Deficiency, 98 J. Clin. Invest. 2167 (1996).
Zeitlin, P., Novel Pharmacologic Therapies for Cystic Fibrosis, 103 J. Clinical Investigation 447 (1999).
Ahrens, M. et al. (Jan. 2001). "Consensus Statement From a Conference for the Management of Patients With Urea Cycle Disorders." *Supp. Journal of Pediatrics* 138 (1):S1-S5.

(56) References Cited

OTHER PUBLICATIONS

Lee, B. et al. (Aug. 2008). "Preliminary Data on Adult Patients with Urea Cycle Disorders (UCD) in an Open-Label, Swirch-Over, Dose Escalation Study Comparing a New Ammonia Scavenger, Glyceryl Tri (4-Phenylbutyrate) [HPN-100], to Buphenyl® (Sodium Phenylbutyrate [PBA])", *abstract presented at SSSIEM 2008*, Lisbon, Portugal, one page.

Lee, B. et al. (Aug. 2008), "Preliminary Data on Adult Patients with Urea Cycle Disorders (UCD) in An Open-Label, Swirch-Over, Dose Escalation Study Comparing a New Ammonia Scavenger, Glyceryl Tri (4-Phenylbutyrate) [HPN-100], to Buphenyl® (Sodium Phenylbutyrate [PBA])", *presented at SSIEM 2008*, Lisbon, Portugal, Poster, one page.

METHODS OF THERAPEUTIC MONITORING OF PHENYLACETIC ACID PRODRUGS

RELATED APPLICATIONS

The present application claims priority to U.S. Provisional Application No. 61/636,256, filed Apr. 20, 2012, the disclosure of which is incorporated by reference herein in its entirety, including drawings.

BACKGROUND

Nitrogen retention disorders associated with elevated ammonia levels include urea cycle disorders (UCDs), hepatic encephalopathy (HE), and advanced kidney disease or kidney failure, often referred to as end-stage renal disease (ESRD).

UCDs include several inherited deficiencies of enzymes or transporters necessary for the synthesis of urea from ammonia, including enzymes involved in the urea cycle. The urea cycle is depicted in FIG. 1, which also illustrates how certain ammonia-scavenging drugs act to assist in elimination of excessive ammonia. With reference to FIG. 1, N-acetyl glutamine synthetase (NAGS)-derived N-acetylglutamate binds to carbamyl phosphate synthetase (CPS), which activates CPS and results in the conversion of ammonia and bicarbonate to carbamyl phosphate. In turn, carbamyl phosphate reacts with ornithine to produce citrulline in a reaction mediated by ornithine transcarbamylase (OTC). A second molecule of waste nitrogen is incorporated into the urea cycle in the next reaction, mediated by arginosuccinate synthetase (ASS), in which citrulline is condensed with aspartic acid to form argininosuccinic acid. Argininosuccinic acid is cleaved by argininosuccinic lyase (ASL) to produce arginine and fumarate. In the final reaction of the urea cycle, arginase (ARG) cleaves arginine to produce ornithine and urea. Of the two atoms of nitrogen incorporated into urea, one originates from free ammonia ($NH_4^+$) and the other from aspartate. UCD individuals born with no meaningful residual urea synthetic capacity typically present in the first few days of life (neonatal presentation). Individuals with residual function typically present later in childhood or even in adulthood, and symptoms may be precipitated by increased dietary protein or physiological stress (e.g., intercurrent illness). For UCD patients, lowering blood ammonia is the cornerstone of treatment.

HE refers to a spectrum of neurologic signs and symptoms believed to result from hyperammonemia, which frequently occur in subjects with cirrhosis or certain other types of liver disease. HE is a common manifestation of clinically decompensated liver disease and most commonly results from liver cirrhosis with diverse etiologies that include excessive alcohol use, hepatitis B or C virus infection, autoimmune liver disease, or chronic cholestatic disorders such as primary biliary cirrhosis. Patients with HE typically show altered mental status ranging from subtle changes to coma, features similar to patients with UCDs. It is believed that an increase in blood ammonia due to dysfunctional liver in detoxifying dietary protein is the main pathophysiology associated with HE (Ong 2003).

ESRD results from a variety of causes including diabetes, hypertension, and hereditary disorders. ESRD is manifested by accumulation in the bloodstream of substances normally excreted in the urine, including but not limited to urea and creatinine. This accumulation in the bloodstream of substances, including toxins, normally excreted in the urine is generally believed to result in the clinical manifestations of ESRD, sometimes referred to also as uremia or uremic syndrome. ESRD is ordinarily treated by dialysis or kidney transplantation. To the extent that urea, per se, contributes to these manifestations and that administration of a phenylacetic (PAA) prodrug may decrease synthesis of urea (see, e.g., Brusilow 1993) and hence lower blood urea concentration, PAA prodrug administration may be beneficial for patients with ESRD.

Subjects with nitrogen retention disorders whose ammonia levels and/or symptoms are not adequately controlled by dietary restriction of protein and/or dietary supplements are generally treated with nitrogen scavenging agents such as sodium phenylbutyrate (NaPBA, approved in the United States as BUPHENYL® and in Europe as AMMONAPS®), sodium benzoate, or a combination of sodium phenylacetate and sodium benzoate (AMMONUL®). These are often referred to as alternate pathway drugs because they provide the body with an alternate pathway to urea for excretion of waste nitrogen (Brusilow 1980; Brusilow 1991). NaPBA is a PAA prodrug. Another nitrogen scavenging drug currently in development for the treatment of nitrogen retention disorders is glyceryl tri-[4-phenylbutyrate] (HPN-100), which is described in U.S. Pat. No. 5,968,979. HPN-100, which is commonly referred to as GT4P or glycerol PBA, is a prodrug of PBA and a pre-prodrug of PAA. The difference between HPN-100 and NaPBA with respect to metabolism is that HPN-100 is a triglyceride and requires digestion, presumably by pancreatic lipases, to release PBA (McGuire 2010), while NaPBA is a salt and is readily hydrolyzed after absorption to release PBA.

HPN-100 and NaPBA share the same general mechanism of action: PBA is converted to PAA via beta oxidation, and PAA is conjugated enzymatically with glutamine to form phenylacetylglutamine (PAGN), which is excreted in the urine. The structures of PBA, PAA, and PAGN are set forth below:

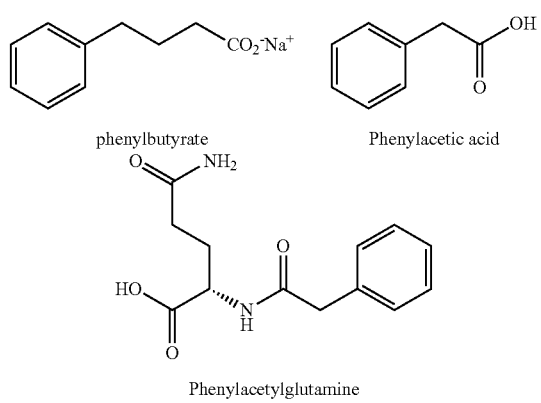

The clinical benefit of NaPBA and HPN-100 with regard to nitrogen retention disorders derives from the ability of PAGN to effectively replace urea as a vehicle for waste nitrogen excretion and/or to reduce the need for urea synthesis (Brusilow 1991; Brusilow 1993). Because each glutamine contains two molecules of nitrogen, the body rids itself of two waste nitrogen atoms for every molecule of PAGN excreted in the urine. Therefore, two equivalents of nitrogen are removed for each mole of PAA converted to PAGN. PAGN represents the predominant terminal metabolite, and one that is stoichiometrically related to waste nitrogen removal, a measure of efficacy in the case of nitrogen retention states.

In addition to nitrogen retention states, PAA prodrugs may be beneficial in a variety of other disorders for which PBA and/or PAA are believed to modify gene expression and/or exert post-translational effects on protein function. In the case of maple syrup urine disease (MSUD, also known as branched-chain ketoaciduria), for example, the apparently beneficial effect of NaPBA in lowering plasma levels of branched chain amino acids is reported to be mediated by PBA-induced inhibition of the kinase that regulates activity of branched chain alpha-keto acid dehydrogenase complex or BCKDC. BCKDC is the enzyme that normally breaks down branched-chain amino acids and is genetically defective in MSUD patients (Bruneti-Pieri 2011). Similarly, the putative beneficial effects of PAA prodrugs for the treatment of cancer (Chung 2000), neurodegenerative diseases (Ryu 2005), and sickle cell disease (Perrine 2008) all involve alteration of gene expression and/or post-translational effects on protein function via PBA and/or PAA.

Numerous publications reports adverse events following administration of PBA and/or PAA (Mokhtarani 2012), and PAA is reported to cause reversible toxicity when present in high levels in circulation. While many of these publications have not recorded PAA blood levels and/or temporally correlated adverse events with PAA levels, toxicities such as nausea, headache, emesis, fatigue, weakness, lethargy, somnolence, dizziness, slurred speech, memory loss, confusion, and disorientation have been shown to be temporally associated with PAA levels ranging from 499-1285 µg/mL in cancer patients receiving PAA intravenously, and these toxicities have been shown to resolve with discontinuation of PAA administration (Thiebault 1994; Thiebault 1995). Therefore, when administering PAA prodrugs for treatment of nitrogen retention disorders and other conditions, it is important to optimize dosing so as to achieve the desired therapeutic effect while minimizing the risk of PAA associated toxicity.

SUMMARY

Provided herein is a clinically practical approach for utilizing and interpreting blood levels of PAA and PAGN to adjust the dose of a PAA prodrug in order to minimize the risk of toxicities and maximize drug effectiveness.

Provided herein in certain embodiments are methods of treating a nitrogen retention disorder or a condition for which PAA prodrug administration is expected to be beneficial in a subject comprising the steps of administering a first dosage of a PAA prodrug, measuring plasma PAA and PAGN levels, calculating a plasma PAA:PAGN ratio, and determining whether the PAA prodrug dosage needs to be adjusted based on whether the PAA:PAGN ratio falls within a target range. In certain embodiments, the target range is 1 to 2.5, 1 to 2, 1 to 1.5, 1.5 to 2, or 1.5 to 2.5. In certain embodiments, a PAA:PAGN ratio above the target range indicates that the dosage of the PAA prodrug needs to be decreased. In other embodiments, a PAA:PAGN ratio above the target range indicates that the dosage may need to be decreased, with the final determination of whether to decrease the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio below the target range indicates that the dosage of the PAA prodrug needs to be increased. In other embodiments, a PAA:PAGN ratio below the target range indicates that the dosage may need to be increased, with the final determination of whether to increase the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio that is within the target range but within a particular subrange (e.g., 1 to 1.5 or 2 to 2.5 where the target range is 1 to 2.5) indicates that the dosage of the PAA prodrug does not need to be adjusted, but that the subject needs to be subjected to more frequent monitoring. In certain embodiments, the methods further comprise a step of administering an adjusted second dosage if such an adjustment is determined to be necessary based on the PAA:PAGN ratio and, optionally, other characteristics of the subject. In other embodiments, the methods further comprise a step of administering a second dosage that is the same as or nearly the same as the first dosage if no adjustment in dosage is deemed to be necessary. In certain embodiments, the nitrogen retention disorder is UCD, HE, or ESRD. In certain embodiments, the condition for which PAA prodrug administration is expected to be beneficial is cancer, a neurodegenerative diseases, a metabolic disorder, or sickle cell disease. In certain embodiments, the PAA prodrug is HPN-100 or NaPBA. In certain embodiments, measurement of plasma PAA and PAGN levels takes place after the first dosage of the PAA prodrug has had sufficient time to reach steady state, such as at 48 hours to 1 week after administration.

Provided herein in certain embodiments are methods of treating a nitrogen retention disorder or a condition for which PAA prodrug administration is expected to be beneficial in a subject who has previously received a first dosage of PAA prodrug comprising the steps of measuring plasma PAA and PAGN levels, calculating a plasma PAA:PAGN ratio, and determining whether the PAA prodrug dosage needs to be adjusted based on whether the PAA:PAGN ratio falls within a target range. In certain embodiments, the target range is 1 to 2.5, 1 to 2, 1 to 1.5, 1.5 to 2, or 1.5 to 2.5. In certain embodiments, a PAA:PAGN ratio above the target range indicates that the dosage of the PAA prodrug needs to be decreased. In other embodiments, a PAA:PAGN ratio above the target range indicates that the dosage may need to be decreased, with the final determination of whether to decrease the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio below the target range indicates that the dosage of the PAA prodrug needs to be increased. In other embodiments, a PAA:PAGN ratio below the target range indicates that the dosage may need to be increased, with the final determination of whether to increase the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio that is within the target range but within a particular subrange (e.g., 1 to 1.5 or 2 to 2.5 where the target range is 1 to 2.5) indicates that the dosage of the PAA prodrug does not need to be adjusted, but that the subject needs to be subjected to more frequent monitoring. In certain embodiments, the methods further comprise a step of administering an adjusted second dosage if such an adjustment is determined to be necessary based on the PAA:PAGN ratio and, optionally, other characteristics of the subject. In other embodiments, the methods further comprise a step of administering a second dosage that is the same as or nearly the same as the first dosage if no adjustment in dosage is deemed to be necessary. In certain embodiments, the nitrogen retention disorder is UCD, HE, or ESRD. In certain embodiments, the condition for which PAA prodrug administration is expected to be beneficial is cancer, a neurodegenerative diseases, a metabolic disorder, or sickle cell disease. In certain embodiments, measurement of plasma PAA and PAGN levels takes place after the first dosage of the PAA prodrug has had sufficient time to reach steady state, such as at 48 hours to 1 week after administration.

Provided herein in certain embodiments are methods of adjusting the dosage of a PAA prodrug to be administered to a subject comprising the steps of administering a first dosage of a PAA prodrug, measuring plasma PAA and PAGN levels, calculating a plasma PAA:PAGN ratio, and determining whether the PAA prodrug dosage needs to be adjusted based on whether the PAA:PAGN ratio falls within a target range. In certain embodiments, the target range is 1 to 2.5, 1 to 2, 1 to 1.5, 1.5 to 2, or 1.5 to 2.5. In certain embodiments, a PAA:PAGN ratio above the target range indicates that the dosage of the PAA prodrug needs to be decreased. In other embodiments, a PAA:PAGN ratio above the target range indicates that the dosage may need to be decreased, with the final determination of whether to decrease the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio below the target range indicates that the dosage of the PAA prodrug needs to be increased. In other embodiments, a PAA:PAGN ratio below the target range indicates that the dosage may need to be increased, with the final determination of whether to increase the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio that is within the target range but within a particular subrange (e.g., 1 to 1.5 or 2 to 2.5 where the target range is 1 to 2.5) indicates that the dosage of the PAA prodrug does not need to be adjusted, but that the subject needs to be subjected to more frequent monitoring. In certain embodiments, the methods further comprise a step of administering an adjusted second dosage if such an adjustment is determined to be necessary based on the PAA:PAGN ratio and, optionally, other characteristics of the subject. In other embodiments, the methods further comprise a step of administering a second dosage that is the same as or nearly the same as the first dosage if no adjustment in dosage is deemed to be necessary. In certain embodiments, measurement of plasma PAA and PAGN levels takes place after the first dosage of the PAA prodrug has had sufficient time to reach steady state, such as at 48 hours to 1 week after administration.

Provided herein in certain embodiments are methods of determining whether a first dosage of a PAA prodrug can be safely administered to a subject comprising the steps of administering the first dosage of a PAA prodrug, measuring plasma PAA and PAGN levels, calculating a plasma PAA:PAGN ratio, and determining whether the first dosage can be safely administered based on whether the PAA:PAGN ratio falls above a target range. In certain embodiments, the target range is 1 to 2.5, 1 to 2, 1 to 1.5, 1.5 to 2, or 1.5 to 2.5. In certain embodiments, a PAA:PAGN ratio above the target range indicates that the first dosage is unsafe and needs to be decreased. In other embodiments, a PAA:PAGN ratio above the target range indicates that the first dosage is potentially unsafe and may need to be decreased, with the final determination of whether to decrease the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio that is within the target range but within a particular subrange (e.g., 2 to 2.5 where the target range is 1 to 2.5) indicates that the first dosage is likely safe, but that the subject needs to be subjected to more frequent monitoring. In certain embodiments, the methods further comprise a step of administering an adjusted second dosage if such an adjustment is determined to be necessary based on the PAA:PAGN ratio and, optionally, other characteristics of the subject. In certain embodiments, measurement of plasma PAA and PAGN levels takes place after the first dosage of the PAA prodrug has had sufficient time to reach steady state, such as at 48 hours to 1 week after administration.

Provided herein in certain embodiments are methods of determining whether a first dosage of a PAA prodrug is likely to be effective for treating a nitrogen retention disorder or another disorder for which PAA prodrug administration is expected to be beneficial comprising the steps of administering the first dosage of a PAA prodrug, measuring plasma PAA and PAGN levels, calculating a plasma PAA:PAGN ratio, and determining whether the first dosage is likely to be effective based on whether the PAA:PAGN ratio falls below a target range. In certain embodiments, the target range is 1 to 2.5, 1 to 2, 1 to 1.5, 1.5 to 2, or 1.5 to 2.5. In certain embodiments, a PAA:PAGN ratio below the target range indicates that the first dosage is unlikely to be effective needs to be increased. In other embodiments, a PAA:PAGN ratio below the target range indicates that the first dosage is potentially ineffective and may need to be increased, with the final determination of whether to increase the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio that is within the target range but within a particular subrange (e.g., 1 to 1.5 where the target range is 1 to 2.5) indicates that the first dosage is likely effective, but that the subject needs to be subjected to more frequent monitoring. In certain embodiments, the methods further comprise a step of administering an adjusted second dosage if such an adjustment is determined to be necessary based on the PAA:PAGN ratio and, optionally, other characteristics of the subject. In certain embodiments, measurement of plasma PAA and PAGN levels takes place after the first dosage of the PAA prodrug has had sufficient time to reach steady state, such as at 48 hours to 1 week after administration.

In certain embodiments, methods are provided for optimizing the therapeutic efficacy of a PAA prodrug in a subject who has previously been administered a first dosage of PAA prodrug comprising the steps of measuring plasma PAA and PAGN levels, calculating a plasma PAA:PAGN ratio, and determining whether the PAA prodrug dosage needs to be adjusted based on whether the PAA:PAGN ratio falls within a target range. In certain embodiments, the target range is 1 to 2.5, 1 to 2, 1 to 1.5, 1.5 to 2, or 1.5 to 2.5. In certain embodiments, a PAA:PAGN ratio above the target range indicates that the dosage of the PAA prodrug needs to be decreased. In other embodiments, a PAA:PAGN ratio above the target range indicates that the dosage may need to be decreased, with the final determination of whether to decrease the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio below the target range indicates that the dosage of the PAA prodrug needs to be increased. In other embodiments, a PAA:PAGN ratio below the target range indicates that the dosage may need to be increased, with the final determination of whether to increase the dosage taking into account other characteristics of the subject such as biochemical profile or clinical characteristics such as target nitrogen excretion, actual nitrogen excretion, symptom severity, disorder duration, age, or overall health. In certain embodiments, a PAA:PAGN ratio that is within the target range but within a particular subrange (e.g., 1 to 1.5 or 2 to 2.5 where the target range is 1 to 2.5) indicates that the dosage of the PAA prodrug does not need to be adjusted, but that the subject needs to be subjected to more frequent monitoring. In certain embodiments, the methods further comprise a step of administering an adjusted second dosage if such an adjustment is determined to be necessary based on the PAA:PAGN ratio and, optionally, other characteristics of the subject. In other embodiments, the methods further comprise a step of administering a second dosage that is the same as or nearly the same as the first dosage if no adjustment in dosage is deemed to be necessary. In certain embodiments, measurement of plasma PAA and PAGN levels takes place after the first dosage of the PAA prodrug has had sufficient time to reach steady state, such as at 48 hours to 1 week after administration.

In certain embodiments, methods are provided for obtaining a plasma PAA:PAGN ratio within a target range in a subject comprising the steps of administering a first dosage of a PAA prodrug, measuring plasma PAA and PAGN levels, calculating a plasma PAA:PAGN ratio, and determining whether the PAA:PAGN ratio falls within the target range. If the PAA:PAGN ratio does not fall within the target range, an adjusted second dosage is administered, and these steps are repeated until a plasma PAA:PAGN ratio falling within the target range is achieved. In certain embodiments, the target range is 1 to 2.5, 1 to 2, 1 to 1.5, 1.5 to 2, or 1.5 to 2.5. In certain embodiments, a PAA:PAGN ratio above the target range indicates that the dosage of the PAA prodrug needs to be decreased and a PAA:PAGN ratio below the target range indicates that the dosage of the PAA prodrug needs to be increased. In certain embodiments, measurement of plasma PAA and PAGN levels takes place after the first dosage of the PAA prodrug has had sufficient time to reach steady state, such as at 48 hours to 1 week after administration.

DETAILED DESCRIPTION

Figure 1:
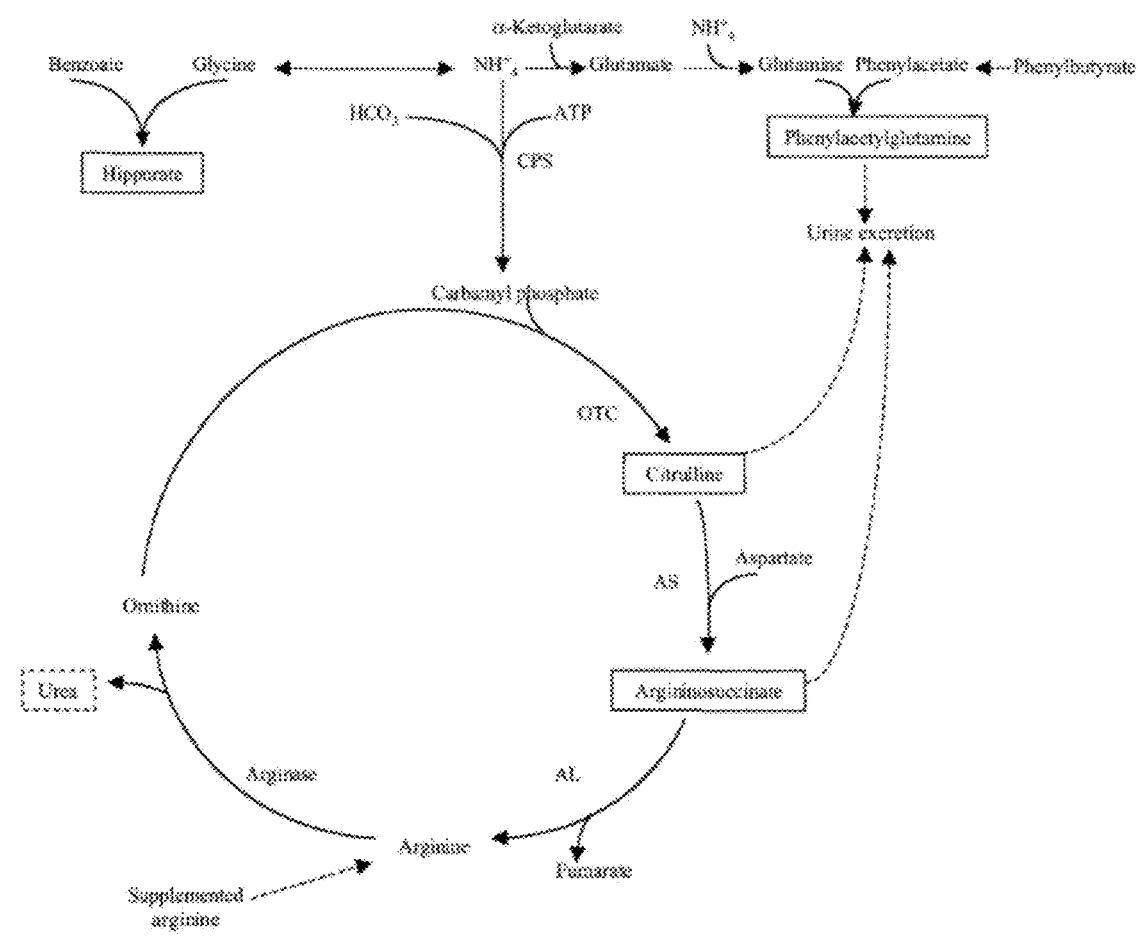
FIG. 1: Urea cycle.
Figure 2A:
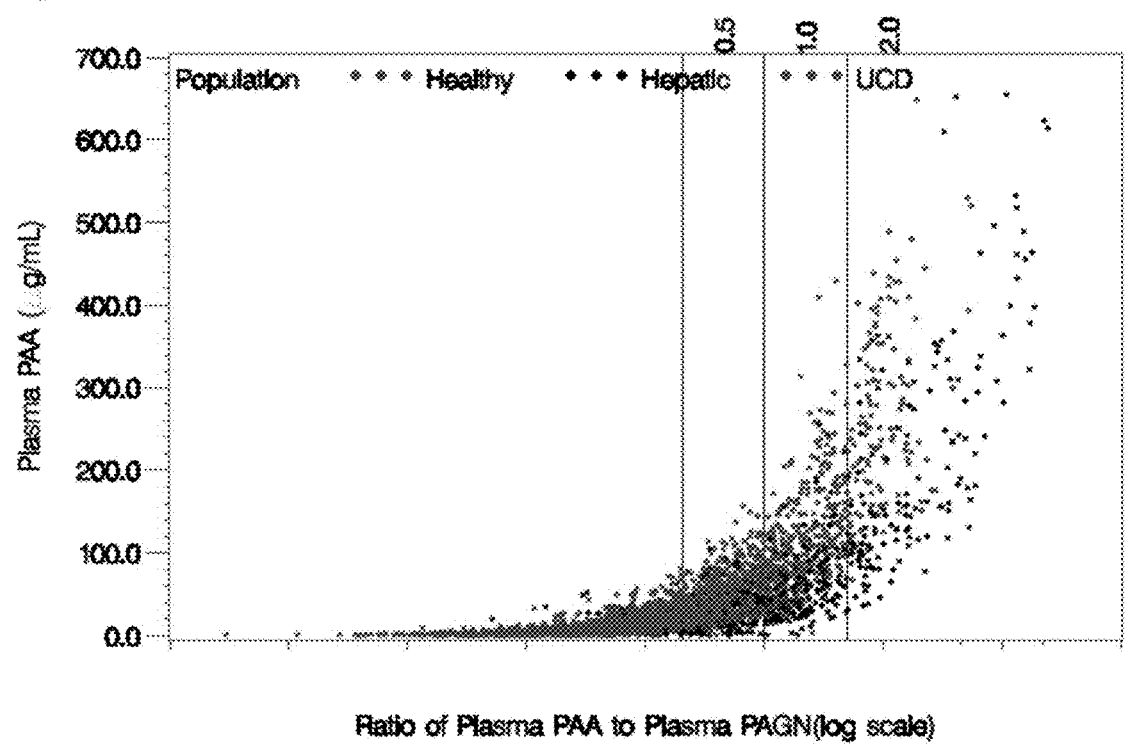
FIG. 2: Plasma PAA levels versus plasma PAA:PAGN ratio in (A) all subjects combined (healthy adults, patients age 2 months and above with UCDs, and patients with cirrhosis), (B) patients age 2 months and above with UCDs, and (C) patients with cirrhosis.
Figure 2B:
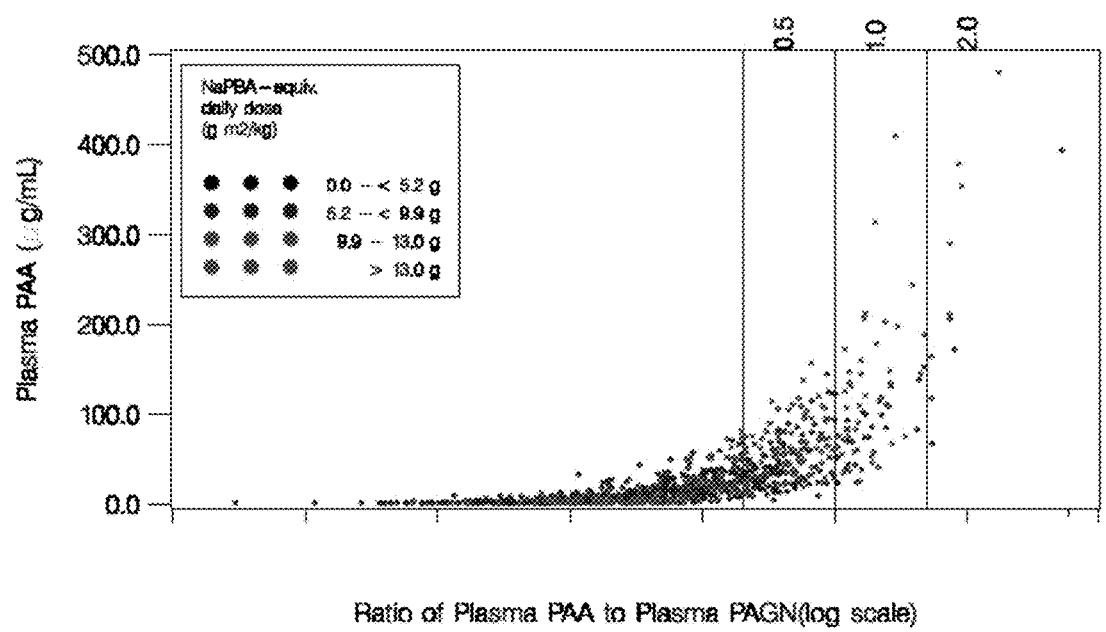
Figure 2C:
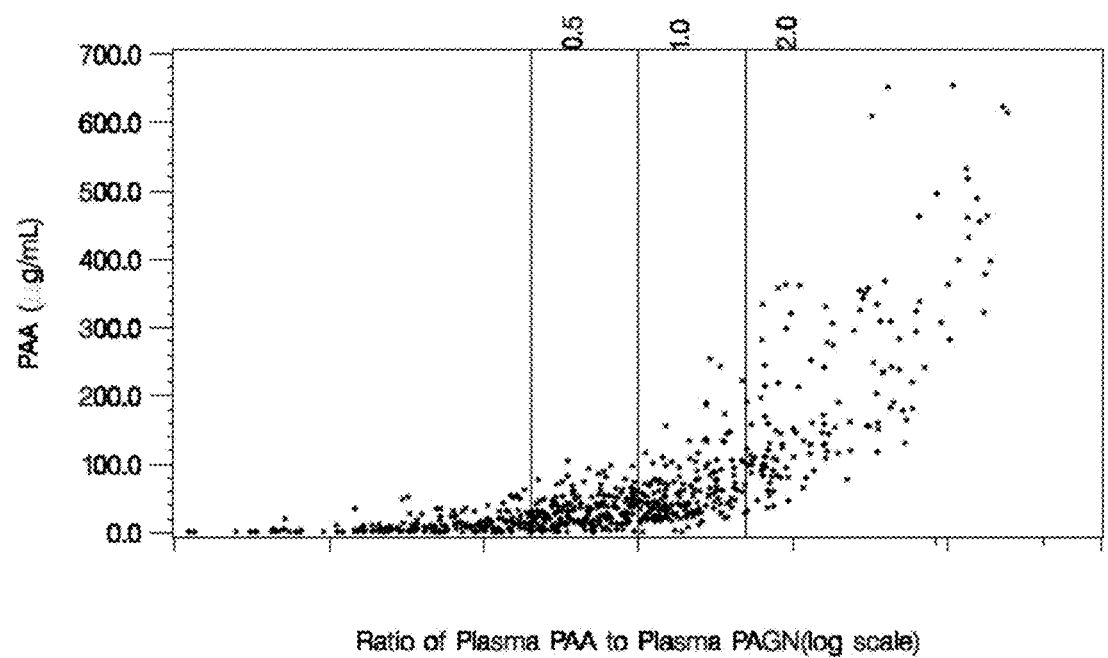

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

The enzymes responsible for beta oxidation of PBA to PAA are present in most cell types capable of utilizing fatty acids as energy substrates, and the widespread distribution of these enzymes presumably accounts for the rapid and essentially complete conversion of PBA to PAA. However, the enzymes that conjugate PAA with glutamine to form PAGN are found primarily in the liver and to a lesser extend in kidneys (Moldave 1957). Therefore, the conversion of PAA to PAGN may be affected under several circumstances, including the following: a) if conjugation capacity is saturated (e.g., by high doses of PAA prodrug); b) if conjugation capacity is compromised (e.g., by severe hepatic and/or renal dysfunction); c) if the substrate (glutamine) for PAA to PAGN conjugation is rate limiting; d) genetically determined variability (i.e., polymorphisms) in the enzymes responsible for PAA to PAGN conversion, or e) in young children, since the capacity to convert PAA to PAGN varies with body size measured as body surface area (Monteleone 2012). The presence of any one of these conditions may lead to accumulation of PAA in the body, which causes reversible toxicity.

The goal of PAA prodrug administration in subjects with nitrogen retention disorders is to provide a sufficient dosage to obtain a desired level of nitrogen removal while avoiding excess build-up of PAA. The goal of PAA prodrug administration in patients without a nitrogen retention disorder (e.g., a neurodegenerative disease) is to achieve circulating metabolite levels necessary to produce a clinical benefit by alteration of gene expression and/or protein folding or function. However, there are several difficulties associated with determining the proper dosage in patients with nitrogen retention disorders.

Plasma PAA and PAGN levels are affected by various factors, including timing of the blood draw in relation to drug administration, hepatic function, availability of metabolizing enzymes, and availability of substrates required for metabolism. A random PAA level drawn during an outpatient visit to determine if levels are in the toxicity range without considering concomitant PAGN level is insufficient to inform dosing. First, PAA levels vary many-fold over the course of the day, fluctuating a great deal between peak and trough levels. For example, in the Hyperion pivotal study evaluating HPN-100 for use in treating adult UCD (Study ID HPN-100-006, Clinical Trials ID NCT00992459), serial blood samples were obtained for PK studies over a 24 hour period during which subjects were receiving HPN-100 or NaPBA. The fluctuation index for PAA over a 24 hour period, which represents the fluctuation between maximum concentration (typically observed after the last daily dose or at approximately 12 hours) and minimum concentration (typically observed in the morning after overnight fasting or at 0 hours), indicated a very high degree of variability (2150% for NaPBA and 1368% for HPN-100). Therefore, a single plasma PAA level may not be representative of the highest PAA level a patient may experience during the day. Second, a high plasma PAA level may only be indicative of the high doses a subject is receiving rather than a point of concern if the subject is effectively conjugating PAA with glutamine to form PAGN. Therefore, basing dose adjustment on only on a high PAA level without considering concomitant plasma PAGN level may result in unnecessary dose reduction and under-treatment of the patient. Conversely, a PAA level seemingly below the levels associated with toxicity might be taken as an indication of satisfactory dosing without appreciating the fact that the concomitant PAGN level may not be proportional to PAA, indicating that PAA is not being efficiently utilized and may be accumulating.

Previous studies have shown that conversion of PAA to PAGN is a saturable process that varies considerably among individuals (see, e.g., Monteleone 2012), and that patients with hepatic impairment have higher PAA levels than patients without hepatic impairment (Ghabril et al., "Glycerol phenylbutyrate (GPD) administration in patients with cirrhosis and episodic hepatic encephalopathy (HE)," submitted to Digestive Disease Week, 2012). If PAGN formation is affected by any of the above factors, PAA will be accumulated and waste nitrogen may not be removed from the body. Previous studies have also shown that a small proportion of individuals, including both healthy adults ad patients with UCDs or HE, have higher PAA levels than the remainder of the population, presumably due to individual differences in conjugating PAA to PAGN, and that PAA levels fluctuate many-fold during the day depending on the dose and the timing of blood sample relative to the last dose so that a single plasma level may not be informative (Lee 2010; Lichter 2011).

Although the goal of PAA prodrug therapy for nitrogen retention disorders is to achieve ammonia levels within a normal limit, there is no correlation between plasma PAA levels and blood ammonia. Nitrogen retention disorder subjects are normally "dosed to effect," meaning that subjects with absent or severely deficient urea synthetic capacity require higher doses of PAA prodrugs than do mildly deficient UCD patients. These higher dosages are generally associated with higher PAA levels, such that the conventional PK/PD response (higher active moiety, i.e., PAA, correlates with lower harmful substance, i.e., ammonia) does not apply. Therefore, there is no single target plasma PAA level that can be applied to patients with UCDs or other nitrogen retention disorders based on their blood ammonia.

Patients with severe hepatic impairment are at increased risk of PAA accumulation due to inadequate levels of PAA conjugating enzymes if treated with PAA-prodrugs. UCD patients without hepatic impairment whose PAA conjugating enzymes are readily saturated are also at increased risk of PAA accumulation if treated with PAA-producing compounds. Other patients without nitrogen retention are at increased risk of PAA accumulation due to limited availability of glutamine as the substrate to form PAGN if treated with PAA-producing compounds, which accumulates in patients with nitrogen retention states.

WO09/134,460 and WO10/025,303 disclose methods for determining an effective dosage of a PAA prodrug based on urinary PAGN levels, which was found to be a more reliable indictor of effective dosage than plasma levels of PAA or other metabolites. Although such measurements are highly useful for evaluating waste nitrogen removal, they do not provide complete information regarding a subject's ability to utilize the prodrug.

Since PAA, PAGN, and ammonia levels do not provide the information necessary to determine whether a subject is effectively converting PBA to PAGN (i.e., effectively utilizing the PAA prodrug), there is a need for improved methods of adjusting PAA prodrug dosage and incorporating such adjustments into methods of treating nitrogen retention disorders.

As disclosed herein, plasma PAA:PAGN ratio has been found to provide an unexpectedly accurate measure of PAA prodrug metabolism in subjects with nitrogen retention disorders and/or hepatic impairment. It was found that subjects who can readily convert PAA to PAGN and have not reached the saturation point with respect to PAA to PAGN conversion will have a plasma PAA:PAGN ratio of 2.5 or below (when both are measured in µg/mL), and that subjects with PAA:PAGN ratios above 2.5 have a significantly higher chance of experience a PAA level above 400 µg/mL or 500 µg/mL over a 24 hour period. A PAA/PAGN ratio of less than 2.5 was associated primarily with healthy adult or adolescent subjects and normal liver function, with subjects having a ratio below 2.5 exhibiting a 1% probability of experiencing a PAA level greater than 400 µg/mL and almost no chance of exhibiting a PAA level greater than 500 µg/mL at any point during a 24 hour period. A ratio greater than 2.5, on the other hand, was generally seen in subjects with moderate hepatic impairment, a subset of healthy subjects or UCD patients with relatively lower saturation point and difficulty conjugating PAA to form PAGN, and patients with a low body surface area. Subjects with a ratio greater than 2.5, on the other hand, exhibited a 20-36% likelihood of experiencing a PAA level greater than 400 µg/mL during the day, and an approximately 10% likelihood of experiencing a PAA level of 500 µg/L or greater. In subjects with a ratio greater than 3, the likelihood of experiencing a PAA level higher than 500 µg/mL increased to as high as 25%. These results show that a plasma PAA:PAGN ratio exceeding 2.5 in a patient with unexplained neurological adverse events and normal ammonia indicates that dosage adjustment should be considered. Thus, plasma PAA:PAGN ratio provides a clinically useful surrogate for evaluating the efficiency of PAA to PAGN conversion.

Plasma PAA:PAGN ratio indicates whether a PAA prodrug is being effectively utilized and scavenging nitrogen, and therefore provides an indirect and simple measure of saturation of conjugating enzymes, availability of substrate, and possible effect of hepatic or renal impairment on this process. Calculating this ratio will allow effective treatment and dose adjustment in subjects with known hepatic impairment, subjects presenting with signs and symptoms overlapping between hyperammonemia and PAA toxicities, and subjects who are not clinically controlled despite increasing the dosage of drugs.

One of ordinary skill in the art would generally not consider the ratio of an active metabolite such as PAA to a terminal metabolite such as PAGN when making therapeutic decisions because they would expect that higher levels of the active metabolite would result in a proportionately higher response (as measured by PAGN production) and increased efficacy (i.e., waste nitrogen removal). However, the results provided herein show that the use of plasma PAA:PAGN ratios to evaluate and adjust PAA prodrug dosage is unexpectedly superior to the use of PAA or PAGN levels alone. Once a subject exceeds a specific PAA:PAGN ratio, there is a high likelihood that they are not effectively utilizing the active moiety and that further increasing PAA prodrug dosage may not increase efficacy and may actually result in PAA accumulation and toxicity.

Based on these findings, methods are provided herein for treating nitrogen retention disorders and evaluating and adjusting the dosage of a PAA prodrug based on plasma PAA:PAGN ratio. Generally, these methods comprise steps of measuring plasma PAA and PAGN levels, calculating the PAA:PAGN ratio, and determining whether the ratio falls within a target range, with this determination being used at least in part to decide whether to adjust PAA prodrug dosage. In these methods, PAA:PAGN ratio can be used to ensure that urinary PAGN output, plasma ammonia concentration, and/or PAA levels fall within a predefined target range. Such methods represent an improvement over previously developed methods for evaluating PAA prodrug dosage and efficacy in that they allow for more accurate dosing, greater efficacy, and decreased risk of toxicity associated with PAA accumulation.

Disclosed herein are target ranges for the ratio of plasma PAA to PAGN in subjects who are receiving PAA prodrug therapy. In certain embodiments, a subject exhibiting a PAA:PAGN ratio falling within a target range is classified as properly dosed, meaning that they do not require a PAA prodrug dosage adjustment, while a subject exhibiting a PAA:PAGN ratio falling outside the target range is classified as improperly dosed, meaning that they require an adjustment in PAA prodrug dosage. In certain of these embodiments, a subject exhibiting a plasma PAA:PAGN ratio falling above a target range is classified as requiring a decreased dosage of PAA prodrug, while a subject exhibiting a plasma PAA:PAGN ratio falling below a target range is classified as requiring an increased dosage of PAA prodrug. In other embodiments, a subject exhibiting a plasma PAA:PAGN ratio falling above a target range is classified as requiring a decreased dosage of PAA prodrug, while a subject exhibiting a plasma PAA:PAGN ratio falling below a target range is classified as potentially requiring an increase in PAA prodrug dosage. In still other embodiments, a subject exhibiting a plasma PAA:PAGN ratio falling above a target range is classified as potentially requiring a decreased dosage of PAA prodrug, while a subject exhibiting a plasma PAA:PAGN ratio falling below a target range is classified as potentially requiring an increase in PAA prodrug dosage. In those embodiments where a subject is classified as potentially requiring an increase or decrease in PAA prodrug dosage based on their PAA:PAGN ratio, a decision as to whether to increase or decrease dosage may be based on one or more additional characteristics of the subject such as biochemical profile or clinical characteristics such as target nitrogen excretion, actual nitrogen excretion, symptom severity, disorder duration, age, or overall health.

In certain embodiments, the target range for plasma PAA:PAGN ratio is 1 to 2.5, meaning that a subject exhibiting a PAA:PAGN falling within this range is classified as properly dosed. In other embodiments, the target range for plasma PAA:PAGN ratio is 1 to 2, 1 to 1.5, 1.5 to 2, or 1.5 to 2.5. In certain of those embodiments where the target range is 1 to 2.5, a subject with a PAA:PAGN ratio above 2.5 is classified as requiring a decrease in PAA prodrug dosage, while a subject with a PAA:PAGN ratio falling below 1 is classified as potentially requiring an increase in PAA prodrug dosage. In certain of these embodiments, a subject is necessarily classified as requiring an increase in PAA prodrug dosage if their ratio is below 1. In other embodiments, a subject with a PAA:PAGN ratio of less than 1 is only classified as requiring an increase in PAA prodrug dosage if one or more additional clinical or biochemical characteristics are satisfied (e.g., the subject is exhibiting severe symptoms of a nitrogen retention disorder).

In certain embodiments, the target range for plasma PAA:PAGN ratio may comprise one or more subranges, with subjects falling within different subranges being treated differently despite falling within the target range. For example, where a target range is 1 to 2.5, a subject exhibiting a PAA:PAGN ratio below 1 or above 2.5 may be classified as requiring an adjustment in PAA prodrug dosage. Within the target range, subjects with a PAA:PAGN ratio falling within a particular subrange may be treated as properly dosed, improperly dosed (i.e., requiring a dosage adjustment), or properly dosed but requiring more frequent monitoring. For example, subjects having a PAA:PAGN ratio greater than 2 but not greater than 2.5 may be classified as properly dosed but requiring more frequent monitoring.

In certain embodiments, subrange boundaries or the treatment of subjects falling within a particular subrange will depend in part on a subject's specific characteristics, including for example biochemical profile or clinical characteristics such as target nitrogen excretion, actual nitrogen excretion, symptom severity, disorder duration, age, or overall health. For example, in certain embodiments a first subject with a PAA:PAGN ratio falling within the subrange of 2 to 2.5 may be classified as properly dosed but requiring frequent monitoring, while a second subject falling within the same subrange may be classified as requiring a decreased dosage of PAA prodrug. Similarly, a first subject with a PAA:PAGN ratio falling within the subrange of 1 to 1.5 may be classified as properly dosed but requiring frequent monitoring, while a second subject falling within the same subrange may be classified as requiring an increased dosage of PAA prodrug. For example, a subject who has recently exhibited particularly acute symptoms associated with a particular disorder may be classified as requiring an increased dosage of PAA prodrug when exhibiting a PAA:PAGN ratio of 1 to 1.5, while a subject who is clinically controlled may be classified as properly dosed despite a ratio falling within the same subrange.

In certain embodiments, methods are provided herein for treating a nitrogen retention disorder or a condition for which PAA prodrug administration is expected to be beneficial in a subject that has previously received a first dosage of a PAA prodrug. These methods comprise measuring plasma PAA and PAGN levels, calculating the plasma PAA:PAGN ratio, determining whether the PAA prodrug dosage needs to be adjusted based on whether the PAA:PAGN ratio falls within a target range, and administering a second dosage of the PAA prodrug. In certain embodiments, the target range for PAA:PAGN ratio is 1 to 2.5 or 1 to 2. In certain of these embodiments, the second dosage is greater than the first dosage if the PAA:PAGN ratio is less than 1 (i.e., the dosage is increased) and less than the first dosage if the PAA:PAGN ratio is greater than 2.5 (i.e., the dosage is decreased). In other embodiments, the second dosage may or may not be greater than the first dosage if the PAA:PAGN ratio is less than 1, depending on one or more other characteristics of the subject. In certain embodiments, the second dosage is equal to the first dosage when the PAA:PAGN ratio is 1 to 2.5, i.e., falling within the target range. In certain embodiments, the target range is divided into one or more subranges. In certain of these embodiments, the second dosage may be equal to the first dosage if the PAA:PAGN ratio is 1 to 1.5 or 2 to 2.5, but the subject may be subjected to more frequent monitoring. In certain other embodiments, the second dosage may be greater than the first dosage if the PAA:PAGN ratio is 1 to 1.5 or 1 to 2 and the subject has recently exhibited particularly acute symptoms of a nitrogen retention disorder or another condition for which PAA prodrug administration is expected to be beneficial. Similarly, the second dosage may be less than the first dosage if the PAA:PAGN ratio is greater than 1.5 or 2 but not greater than 2.5, depending on the subject's specific characteristics. In certain embodiments, the increase or decrease in the second dosage versus the first dosage depends on the precise plasma PAA:PAGN ratio. For example, where the plasma PAA:PAGN ratio is only slightly less than 1, the dosage may be increased only slightly, but where the PAA:PAGN ratio is significantly less than 1, the dosage may be increased more. Similarly, the decrease in dosage for subjects exhibiting a ratio above 2.5 may vary depending on how far above 2.5 the ratio extends. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration). In certain embodiments, the above steps may be repeated until a desired plasma PAA:PAGN ratio (e.g., 1 to 2.5 or 1 to 2) is achieved. For example, the methods may comprise measuring plasma PAA and PAGN levels after administration of the second dosage, calculating the plasma PAA:PAGN ratio, determining whether the PAA prodrug dosage needs to be adjusted based on whether the PAA:PAGN ratio falls within the target range, and administering a third dosage of the PAA prodrug.

In certain embodiments, methods are provided for treating a nitrogen retention disorder or a condition for which PAA prodrug administration is expected to be beneficial in a subject that has not previously been administered a PAA prodrug. These methods comprise administering a first dosage of a PAA prodrug, measuring plasma PAA and PAGN levels, calculating the plasma PAA:PAGN ratio, determining whether the PAA prodrug dosage needs to be adjusted based on whether the PAA:PAGN ratio falls within a target range, and administering a second dosage of the PAA prodrug. In certain embodiments, the target range for PAA:PAGN ratio is 1 to 2.5 or 1 to 2. In certain of these embodiments, the second dosage is greater than the first dosage if the PAA:PAGN ratio is less than 1 (i.e., the dosage is increased) and less than the first dosage if the PAA:PAGN ratio is greater than 2.5 (i.e., the dosage is decreased). In other embodiments, the second dosage may or may not be greater than the first dosage if the PAA:PAGN ratio is less than 1, depending on one or more additional characteristics of the subject. In certain embodiments, the second dosage is equal to the first dosage when the PAA:PAGN ratio is 1 to 2.5, i.e., falling within the target range. In certain embodiments, the target range is divided into one or more subranges. In certain of these embodiments, the second dosage may be equal to the first dosage if the PAA:PAGN ratio is 1 to 1.5 or 2 to 2.5, but the subject may be subjected to more frequent monitoring. In certain other embodiments, the second dosage may be greater than the first dosage if the PAA:PAGN ratio is 1 to 1.5 or 1 to 2 and the subject has recently exhibited particularly acute symptoms of a nitrogen retention disorder or another condition for which PAA prodrug administration is expected to be beneficial. Similarly, the second dosage may be less than the first dosage if the PAA:PAGN ratio is greater than 1.5 or 2 but not greater than 2.5, depending on the subject's specific clinical or biochemical characteristics. In certain embodiments, the increase or decrease in the second dosage versus the first dosage depends on the precise plasma PAA:PAGN ratio. For example, where the plasma PAA:PAGN ratio is only slightly less than 1, the dosage may be increased only slightly, but where the PAA:PAGN ratio is significantly less than 1, the dosage may be increased more. Similarly, the decrease in dosage for subjects exhibiting a ratio above 2.5 may vary depending on how far above 2.5 the ratio extends. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration). In certain embodiments, the above steps may be repeated until a desired plasma PAA:PAGN ratio (e.g., 1 to 2.5 or 1 to 2) is achieved. For example, the methods may comprise measuring plasma PAA and PAGN levels after administration of the second dosage, calculating the plasma PAA:PAGN ratio, determining whether the PAA prodrug dosage needs to be adjusted based on whether the PAA:PAGN ratio falls within the target range, and administering a third dosage of the PAA prodrug.

A method of administering a PAA prodrug to a subject with a nitrogen retention disorder or another condition for which PAA prodrug administration is expected to be beneficial. These methods comprise administering a first dosage of the PAA prodrug, measuring plasma PAA and PAGN levels, calculating the plasma PAA:PAGN ratio, determining whether the PAA prodrug dosage needs to be adjusted based on whether the PAA:PAGN ratio falls within a target range, and administering a second dosage of the PAA prodrug. In certain embodiments, the target range for PAA:PAGN ratio is 1 to 2.5 or 1 to 2. In certain of these embodiments, the second dosage is greater than the first dosage if the PAA:PAGN ratio is less than 1 (i.e., the dosage is increased) and less than the first dosage if the PAA:PAGN ratio is greater than 2.5 (i.e., the dosage is decreased). In other embodiments, the second dosage may or may not be greater than the first dosage if the PAA:PAGN ratio is less than 1, depending on one or more additional characteristics of the subject. In certain embodiments, the second dosage is equal to the first dosage when the PAA:PAGN ratio is 1 to 2.5, i.e., falling within the target range. In certain embodiments, the target range is divided into one or more subranges. In certain of these embodiments, the second dosage may be equal to the first dosage if the PAA:PAGN ratio is 1 to 1.5 or 2 to 2.5, but the subject may be subjected to more frequent monitoring. In certain other embodiments, the second dosage may be greater than the first dosage if the PAA:PAGN ratio is 1 to 1.5 or 1 to 2 and the subject has recently exhibited particularly acute symptoms of a nitrogen retention disorder or another condition for which PAA prodrug administration is expected to be beneficial. Similarly, the second dosage may be less than the first dosage if the PAA:PAGN ratio is greater than 1.5 or 2 but not greater than 2.5, depending on the subject's specific biochemical or clinical characteristics. In certain embodiments, the increase or decrease in the second dosage versus the first dosage depends on the precise plasma PAA:PAGN ratio. For example, where the plasma PAA:PAGN ratio is only slightly less than 1, the dosage may be increased only slightly, but where the PAA:PAGN ratio is significantly less than 1, the dosage may be increased more. Similarly, the decrease in dosage for subjects exhibiting a ratio above 2.5 may vary depending on how far above 2.5 the ratio extends. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration). In certain embodiments, the above steps may be repeated until a desired plasma PAA:PAGN ratio (e.g., 1 to 2.5 or 1 to 2) is achieved. For example, the methods may comprise measuring plasma PAA and PAGN levels after administration of the second dosage, calculating the plasma PAA:PAGN ratio, determining whether the PAA prodrug dosage needs to be adjusted based on whether the PAA:PAGN ratio falls within the target range, and administering a third dosage of the PAA prodrug.

In certain embodiments, methods are provided herein for achieving a target plasma PAA:PAGN ratio in a subject with a nitrogen retention disorder or another condition for which PAA prodrug administration is expected to be beneficial. These methods comprise administering a first dosage of a PAA prodrug, measuring plasma PAA and PAGN levels, calculating the plasma PAA:PAGN ratio, determining whether the PAA prodrug dosage needs to be adjusted based on whether the PAA:PAGN ratio falls within a target range, and administering a second dosage of the PAA prodrug based on the PAA:PAGN ratio. If the PAA:PAGN ratio is above the target range, the second dosage is less than the first dosage. If the PAA:PAGN ratio is below the target range, the second dosage is greater than the first dosage. These steps are repeated until a target plasma PAA:PAGN ratio is achieved. In certain embodiments, the target ratio falls within a target range of 1 to 2.5 or 1 to 2. In certain embodiments, the increase or decrease in the second dosage versus the first dosage depends on the precise plasma PAA:PAGN ratio. For example, where the plasma PAA:PAGN ratio is only slightly less than 1, the dosage may be increased only slightly, but where the PAA:PAGN ratio is significantly less than 1, the dosage may be increased more. Similarly, the decrease in dosage for subjects exhibiting a ratio above 2.5 may vary depending on how far above 2.5 the ratio extends. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration).

In certain embodiments, methods are provided for evaluating the dosage of a PAA prodrug in a subject who has previously been administered a first dosage of a PAA prodrug. These methods comprise measuring plasma PAA and PAGN levels, calculating the plasma PAA:PAGN ratio, and determining whether the first dosage of the PAA prodrug is effective based on whether the PAA:PAGN ratio falls within a target range. In certain embodiments, the target range for PAA:PAGN ratio is 1 to 2.5 or 1 to 2. In certain of these embodiments, the first dosage is considered too low if the PAA:PAGN ratio is less than 1, and too high if the PAA:PAGN ratio is greater than 2.5. In other embodiments, the first dosage is considered potentially too low if PAA:PAGN ratio is less than 1, with a final decision depending on one or more additional characteristics of the subject. In certain embodiments, the target range is divided into one or more subranges. In certain of these embodiments, the first dosage is considered potentially effective if the PAA:PAGN ratio is 1 to 1.5 or 2 to 2.5, but the subject may be subjected to more frequent monitoring. In certain other embodiments, the first dosage may be considered too low if the PAA:PAGN ratio is 1 to 1.5 or 1 to 2 and the subject has recently exhibited particularly acute symptoms of a nitrogen retention disorder or another condition for which PAA prodrug administration is expected to be beneficial. Similarly, in certain embodiments the first dosage may be considered too high if the PAA:PAGN ratio is greater than 1.5 or 2 but not greater than 2.5, depending on the subject's specific biochemical or clinical characteristics. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration). In certain embodiments, the methods further comprise a step of administering a second dosage that differs from the first dosage, and in certain of these embodiments the above steps may be repeated until a desired plasma PAA:PAGN ratio (e.g., 1 to 2.5 or 1 to 2) is achieved. For example, the methods may comprise administering a second dosage that differs from the first dosage, measuring plasma PAA and PAGN levels after administration of the second dosage, calculating the plasma PAA:PAGN ratio, and determining whether the second dosage of the PAA prodrug is effective based on whether the PAA:PAGN ratio falls within a target range.

In certain embodiments, methods are provided for adjusting the dosage of a PAA prodrug in a subject who has previously been administered a first dosage of a PAA prodrug. These methods comprise measuring plasma PAA and PAGN levels, calculating the plasma PAA:PAGN ratio, and determining whether to adjust the dosage of the PAA prodrug based on whether the PAA:PAGN ratio falls within a target range. In certain embodiments, the target range for PAA:PAGN ratio is 1 to 2.5 or 1 to 2. In certain of these embodiments where the target range is 1 to 2.5, a PAA:PAGN ratio of less than 1 indicates the PAA prodrug dosage needs to be adjusted upwards, while a PAA:PAGN ratio above 2.5 indicates the PAA prodrug dosage needs to be adjusted downwards. In other embodiments, a PAA:PAGN ratio of less than 1 indicates that the PAA prodrug dosage potentially needs to be adjusted upwards, with a final decision depending on one or more additional characteristics of the subject. In certain embodiments, the target range is divided into one or more subranges. In certain of these embodiments, a PAA:PAGN ratio of 1 to 1.5 or 2 to 2.5 indicates that the dosage need not be adjusted, but that the subject should be subjected to more frequent monitoring. In certain other embodiments, a PAA:PAGN ratio of 1 to 1.5 or 1 to 2 indicates that the dosage needs to be increased when the subject has recently exhibited particularly acute symptoms of a nitrogen retention disorder or another condition for which PAA prodrug administration is expected to be beneficial. Similarly, in certain embodiments a PAA:PAGN ratio greater than 1.5 or 2 but not greater than 2.5 may indicate that the dosage needs to be decreased, depending on the subject's specific biochemical or clinical characteristics. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration). In certain embodiments where a determination is made that the dosage needs to be adjusted, the methods further comprise a step of administering a second dosage that differs from the first dosage, and in certain of these embodiments the above steps may be repeated until a desired plasma PAA:PAGN ratio (e.g., 1 to 2.5 or 1 to 2) is achieved. For example, the methods may comprise administering a second dosage that differs from the first dosage, measuring plasma PAA and PAGN levels after administration of the second dosage, calculating the plasma PAA:PAGN ratio, and determining whether the second dosage of the PAA prodrug needs to be adjusted based on whether the PAA:PAGN ratio falls within a target range. In certain embodiments, the increase or decrease in the second dosage versus the first dosage depends on the precise plasma PAA:PAGN ratio. For example, where the plasma PAA:PAGN ratio is only slightly less than 1, the dosage may be increased only slightly, but where the PAA:PAGN ratio is significantly less than 1, the dosage may be increased more. Similarly, the decrease in dosage for subjects exhibiting a ratio above 2.5 may vary depending on how far above 2.5 the ratio extends.

In certain embodiments, methods are provided for optimizing the therapeutic efficacy of a PAA prodrug for use in treating a nitrogen retention disorder in a subject. These methods comprise measuring plasma PAA and PAGN levels in a subject who has previously been administered a PAA prodrug, calculating the plasma PAA:PAGN ratio, determining whether to adjust the dosage of the PAA prodrug based on whether the PAA:PAGN ratio falls within a target range, and administering an adjusted dosage of the PAA prodrug as necessary. These steps are repeated until the subject exhibits a plasma PAA:PAGN ratio falling within the target range (e.g., 1 to 2.5 or 1 to 2). In certain embodiments where the target range is 1 to 2.5, a plasma PAA:PAGN ratio of less than 1 indicates that the dosage needs to be adjusted upwards, while a ratio greater than 2.5 indicates that the dosage needs to be decreased. In certain embodiments, the target range is divided into one or more subranges. In certain of these embodiments, a PAA:PAGN ratio of 1 to 1.5 or 2 to 2.5 indicates that the dosage does not need to be adjusted, but that the subject should be subjected to more frequent monitoring. In certain other embodiments, a PAA:PAGN ratio of 1 to 1.5 or 1 to 2 indicates that the dosage needs to be increased when the subject has recently exhibited particularly acute symptoms of a nitrogen retention disorder or another condition for which PAA prodrug administration is expected to be beneficial. Similarly, in certain embodiments a PAA:PAGN ratio greater than 1.5 or 2 but not greater than 2.5 may indicate that the dosage needs to be decreased, depending on the subject's specific biochemical or clinical characteristics. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration). In certain embodiments, the magnitude of the increase or decrease in dosage may be based on the precise PAA:PAGN ratio. For example, a PAA:PAGN ratio that is slightly less than 1 may indicate that the dosage needs to be increased slightly, while a ratio significantly less than 1 may indicate the dosage needs to be increased to a greater degree. In certain embodiments, the above steps are repeated until the subject exhibits a PAA:PAGN ratio falling within the target range.

In certain embodiments, methods are provided for determining whether a prescribed first dosage of a PAA prodrug can be safely administered to a subject. These methods comprise administering the prescribed first dosage to the subject, measuring plasma PAA and PAGN levels, calculating the plasma PAA:PAGN ratio, and determining whether the prescribed first dosage is safe for the subject based on whether the PAA:PAGN ratio falls above a target range, wherein a PAA:PAGN ratio falling above the target range indicates that the first dosage cannot be or potentially cannot be safely administered to the subject. In certain embodiments, the target range for PAA:PAGN ratio is 1 to 2.5 or 1 to 2. In certain of these embodiments where the target range is 1 to 2.5, a PAA:PAGN ratio above 2.5 indicates the PAA prodrug dosage is unsafe and needs to be adjusted downwards. In certain embodiments, the target range is divided into one or more subranges. In certain of these embodiments, a PAA:PAGN ratio of 2 to 2.5 indicates that the first dosage is safe, but that the subject should be subjected to more frequent monitoring. In other embodiments, a PAA:PAGN ratio of 2 to 2.5 indicates that the first dosage is potentially unsafe, with a final determination of safety taking into account the subject's specific biochemical or clinical characteristics. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration). In certain embodiments where a determination is made that the first dosage is unsafe and needs to be decreased, the methods further comprise a step of administering a second dosage that is lower than the first dosage, and in certain of these embodiments the above steps may be repeated until a desired plasma PAA:PAGN ratio (e.g., 1 to 2.5 or 1 to 2) is achieved. For example, the methods may comprise administering a second dosage that is lower than the first dosage, measuring plasma PAA and PAGN levels after administration of the second dosage, calculating the plasma PAA:PAGN ratio, and determining whether the second dosage of the PAA prodrug can be safely administered to the subject based on whether the PAA:PAGN ratio falls above a target range.

In certain embodiments, methods are provided for determining whether a prescribed first dosage of a PAA prodrug will be effective for treating a nitrogen retention disorder or another disorder for which PAA prodrug administration is expected to be beneficial. These methods comprise administering the prescribed first dosage to the subject, measuring plasma PAA and PAGN levels, calculating the plasma PAA:PAGN ratio, and determining whether the prescribed first dosage will be effective for the subject based on whether the PAA:PAGN ratio falls below a target range, wherein a PAA:PAGN ratio falling below the target range indicates that the first dosage will not be or potentially will not be effective for treating a disorder. In certain embodiments, the target range for PAA:PAGN ratio is 1 to 2.5 or 1 to 2. In certain of these embodiments where the target range is 1 to 2.5, a PAA:PAGN ratio below 1 indicates the PAA prodrug dosage is unlikely to be effective and needs to be adjusted upwards. In other embodiments, a PAA:PAGN ratio below 1 indicates that the first dosage is potentially ineffective, with a final determination of whether the dosage is likely to be ineffective based on the subject's specific biochemical or clinical characteristics. In certain embodiments, the target range is divided into one or more subranges. In certain of these embodiments, a PAA:PAGN ratio of 1 to 1.5 indicates that the first dosage is likely to be effective, but that the subject should be subjected to more frequent monitoring. In other embodiments, a PAA:PAGN ratio of 1 to 1.5 indicates that the first dosage is potentially ineffective, with a final determination of whether the dosage is likely to be ineffective taking into account the subject's specific biochemical or clinical characteristics. In certain embodiments, measurement of plasma PAA and PAGN ratio takes place after the PAA prodrug has had sufficient time to reach steady state (e.g., 48 hours, 48 to 72 hours, 72 hours to 1 week, 1 week to 2 weeks, or greater than 2 weeks after PAA prodrug administration). In certain embodiments where a determination is made that the first dosage is likely to be ineffective and needs to be increased, the methods further comprise a step of administering a second dosage that is higher than the first dosage, and in certain of these embodiments the above steps may be repeated until a desired plasma PAA:PAGN ratio (e.g., 1 to 2.5 or 1 to 2) is achieved. For example, the methods may comprise administering a second dosage that is higher than the first dosage, measuring plasma PAA and PAGN levels after administration of the second dosage, calculating the plasma PAA:PAGN ratio, and determining whether the second dosage of the PAA prodrug is likely to be ineffective for treating a disorder based on whether the PAA:PAGN ratio falls above a target range.

Provided herein in certain embodiments are methods for monitoring therapy with a PAA prodrug in patients with a nitrogen retention disorder. These methods comprise administering a PAA prodrug to the subject, measuring plasma PAA and PAGN levels, and calculating the plasma PAA:PAGN ratio. In these methods, a PAA:PAGN ratio falling within a target range (e.g., 1 to 2.5 or 1 to 2) indicates that the therapy is effective, while a ratio falling outside this range indicates that the therapy may need to be adjusted. In certain embodiments, the plasma PAA:PAGN ratio is compared to a previously obtained PAA:PAGN ratio from the same subject to evaluate the effectiveness of PAA prodrug administration.

In certain embodiments, the methods provided herein may be used in conjunction with the methods described in WO09/134,460 and WO10/025,303. In these embodiments, urinary PAGN levels may be determined in addition to plasma PAA:PAGN ratio, with both measurements being used to evaluate or adjust PAA prodrug dosage.

A "PAA prodrug" as used herein refers to any drug that contains or is converted to PAA following administration to a subject, or to any pharmaceutically acceptable salt, ester, acid, or derivative thereof. A PAA prodrug may be administered via any route, including oral or parenteral administration. A PAA prodrug may be converted directly to PAA (e.g., a salt or ester of PAA; PBA or a salt or ester thereof such as NaPBA), or it may be converted to PAA via an intermediate (e.g., a pre-prodrug such as HPN-100). Other examples of PAA prodrugs include butyroyloxymethyl-4-phenylbutyrate.

An adjustment to the dosage of a PAA prodrug as discussed herein may refer to a change in the amount of drug per administration (e.g., an increase from a first dosage of 3 mL to a second dosage of 6 mL), a change in the number of administration within a particular time period (e.g., an increase from once a day to twice a day), or any combination thereof.

A "subject in need thereof" as used herein refers to any individual having a condition or suspected of having a condition for which administration of a PAA prodrug is expected to be beneficial. For example, a subject may be an individual with a nitrogen retention disorder or suspected of having a nitrogen retention disorder, including for example UCD, HE, and/or kidney failure/ESRD (Lee 2010; McGuire 2010; Lichter 2011). Likewise, a subject may have or be suspected of having another condition for which PAA prodrug administration is expected to be beneficial, including for example cancer (Thiebault 1994; Thiebault 1995), neurodegenerative disorders such as Huntington's Disease (Hogarth 2007), amyotrophic lateral sclerosis (ALS) (Cudkowicz 2009), and spinal muscular atrophy (SMA) (Mercuri 2004; Brahe 2005), metabolic disorders (e.g., maple syrup urine disease (MSUD) (Bruneti-Pieri 2011), or sickle cell disease (Hines 2008).

A subject that has previously been administered a PAA prodrug may have been administered the drug for any duration of time sufficient to reach steady state. For example, the subject may have been administered the drug over a period of 2 to 7 days, 1 week to 2 weeks, 2 weeks to 4 weeks, 4 weeks to 8 weeks, 8 weeks to 16 weeks, or longer than 16 weeks.

A "PAA prodrug" as used herein refers to any drug that contains or is converted to PAA following administration to a subject, or to any pharmaceutically acceptable salt, ester, acid, or derivative thereof. A PAA prodrug may be administered via any route, including oral or parenteral administration. A PAA prodrug may be converted directly to PAA (e.g., PBA or a salt thereof such as NaPBA), or it may be converted to PAA via an intermediate (e.g., a pre-prodrug such as HPN-100). Other examples of PAA prodrugs include butyroyloxymethyl-4-phenylbutyrate.

An adjustment to the dosage of a PAA prodrug as discussed herein may refer to a change in the amount of drug per administration (e.g., an increase from a first dosage of 3 mL to a second dosage of 6 mL), a change in the number of administration within a particular time period (e.g., an increase from once a day to twice a day), or any combination thereof.

The terms "treat," "treating," or "treatment" as used herein may refer to preventing a disorder, slowing the onset or rate of development of a disorder, reducing the risk of developing a disorder, preventing or delaying the development of symptoms associated with a disorder, reducing or ending symptoms associated with a disorder, generating a complete or partial regression of a disorder, or some combination thereof. For example, where the disorder being treated is a nitrogen retention disorder, "treating" may refer to lowering waste nitrogen levels below a threshold level, preventing waste nitrogen levels from reaching a threshold level, decreasing the likelihood of waste nitrogen levels exceeding a threshold level, reducing or ending symptoms associated with elevated waste nitrogen levels, or a combination thereof.

With regard to the methods of treatment disclosed herein, interpretation of the PAA:PAGN ratio must be performed in the context of the therapeutic objective. For example, in subjects being treated for a nitrogen retention disorder, the therapeutic objective is elimination of waste nitrogen in the form of PAGN. In subjects being treated for other disorders for which PAA prodrug administration is expected to be beneficial (e.g., neurodegenerative disorders, MSUD), the therapeutic objective is safely achieving target plasma levels of PAA and/or PBA.

Any methods known in the art may be used to obtain a plasma blood sample. For example, blood from a subject may be drawn into a tube containing heparin or ethylenediaminetetraacetic acid (EDTA). In certain embodiments, the sample can be placed on ice and centrifuged to obtain plasma within 15 minutes of collection, stored at 2-8° C. (36-46° F.) and analyzed within 3 hours of collection. In other embodiments, the blood plasma sample is snap frozen, stored at ≤−18° C. (≤0° F.) and analyzed at a later time. For example, the sample may be analyzed at 0-12 hours, 12-24 hours, 24-48, 48-96 hours after freezing, or within any other timeframe over which the sample has demonstrated stability. In certain of these embodiments, the blood sample is stored at a temperature between 0-15° C., such as 2-8° C. In other embodiments, the blood sample is stored below 0° C. or below −18° C.

Measurement of PAA and PAGN levels in a plasma sample is carried out using techniques known in the art. For example, PAA and PAGN levels may be measured using liquid chromatography/mass spec analyses.

Any combination of embodiments described herein can be envisioned. Although individual features may be included in different claims, these may be advantageously combined.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Analysis of PAA:PAGN Ratio in UCD and HE Subjects

Plasma PAA and PAGN levels and PAA:PAGN ratio were analyzed in more than 4000 plasma samples obtained from various clinical trials of healthy adults, severely hepatic impaired adults with clinically decompensated Child-Pugh B or C cirrhosis, and UCD patients ages 29 days or older. Healthy and hepatically impaired adults received HPN-100, while UCD subjects received both HPN-100 and NaPBA. Clinical trial populations are summarized in Tables 1 and 2.

TABLE 1

Clinical studies and analysis populations

| Study Group | Description | Demographics | Protocols Included | Analysis Populations |
|---|---|---|---|---|
| 1 | Short-term (<=2-4 weeks) exposure in UCD subjects | Adults and children ages 29 days or greater (N = 81) | UP 1204-003 HPN-100-005SO HPN-100-006 HPN-100-012 | A, B |
| 2 | Long-term exposure in UCD and HE subjects | Adults and children ages 6 years or greater (N = 180) | HPN-100-005SE HPN-100-007 HPN-100-008 Part B | A |
| 3 | Short-term (<=4 weeks) exposure in hepatic impaired subjects | Adults (N = 15) | HPN-100-008 Part A | A, B |
| 4 | Short-term exposure (<=4 weeks) in healthy subjects | Adults (N = 98) | HPN-100-010 | A, B |

TABLE 2

Demographics and number of samples used

| | | No. of subjects | | No. of sample points (Population A) | | No. of time-specific PK sample points (Population B) | |
|---|---|---|---|---|---|---|---|
| | Attribute | Count | Percent | Count | Percent | Count | Percent |
| Population | Healthy | 86 | 17.0 | 2126 | 34.4 | 2126 | 38.5 |
| | Hepatic Encephalopathy (HE) | 103 | 20.4 | 830 | 13.4 | 830 | 15.0 |
| | UCD | 158 | 31.3 | 1616 | 26.1 | 1281 | 23.2 |
| | Total | 347 | 100.0 | 4572 | 100.0 | 4237 | 100.0 |
| Age | 29 days-<6 yrs | 15 | 4.3 | 110 | 2.4 | 110 | 2.6 |
| | 6-<18 yrs | 47 | 13.5 | 373 | 8.2 | 213 | 5.0 |
| | 18+ yrs | 285 | 82.1 | 4089 | 89.4 | 3914 | 92.4 |
| Sex | F | 199 | 57.3 | 2394 | 52.4 | 2152 | 50.8 |
| | M | 148 | 42.7 | 2178 | 47.6 | 2085 | 49.2 |

Analysis Population A consisted of quantifiable levels of PAA and PAGN metabolites derived from all studies described above. All PAA and PAGN levels used for analysis came from blood samples drawn once dosing with NaPBA or HPN-100 had reached steady state. Analysis Population B consisted of quantifiable levels of PAA and PAGN metabolites during studies in which pharmacokinetics were analyzed and for which blood draws were performed over 12 or 24 hours at steady state and for which the timing of the blood sample in relation to dosing was known. Subjects in study groups 1, 3 and 4 above contributed to these points. Analysis Population B was the source of analyses that examined how PAA levels changed with time relative to dosing, where dosing could have been with either NaPBA or HPN-100. To be eligible for Analysis Population B, the time of the blood draw relative to the time of initiation of dosing during the dosing period had to have been recorded.

Data on metabolite levels were pooled across a wide range of age levels—infants, toddlers, children, adolescents, and adults. All children, defined as ages under 18, were UCD patients. The majority of the blood sampling points came from adults (89.4%). Newborn infants (<29 days old) were not studied in any of the clinical trials for the investigational agent HPN-100. The population of blood sampling points were roughly equally divided between female and male (57.3% female, 42.7% male).

To examine the predictive ability of PAA:PAGN ratios, a subject was considered to have achieved a high value of PAA if any PAA value up to 24 hours since initiation of dosing equaled or exceeded 400 µg/mL or equaled or exceeded 500 µg/mL. PAA:PAGN ratios were grouped into one of three categorization schemes: a.) [0-<=2.0], [>2.0], b.) [0-<=2.5, >2.5], c.) [0-<=3.0, >3.0]. The repeated measures categorical outcome was modeled using GEE with a logit link function, ratio category as the independent variable, and SUBJECTID as the repeated measures factor. Confidence intervals for the predicted probabilities were computed by bootstrap estimation of 1000 resamplings of the original data, as detailed in Davison & Hinkley, "Bootstrap Methods and Their Application," Cambridge Univ. Press (1997), pp. 358-362.

Results are summarized in FIGS. 2-5. A striking curvilinear relationship was observed between plasma PAA levels and PAA:PAGN ratio at any given timepoint. FIG. 2A shows the relationship between the ratio of PAA:PAGN concentrations and absolute PAA levels in micrograms per milliliter among blood samples that had quantifiable values for both PAA and PAGN. The ratio axis (i.e. 'X' axis) is plotted on a logarithmic (base e) scale. For ratios less than 1.0, increases in ratio are not associated with correspondingly elevated or increased levels of PAA. Above ratios of 1.0, there is a gradual increase in PAA levels, and a noticeable upswing in PAA levels that begins in the vicinity of a ratio of 2.0. This finding suggests that when the ratio of PAA precursor to PAGN product approaches higher values, the values of PAA are also correspondingly high. This increase in the ratio of precursor (PAA) to product (PAGN) implies ineffective PAA to PAGN conversion, regardless of whether the PAA is derived from HPN-100 or NaPBA.

To determine whether excessive PAA build-up is a function of dosing, the plots mentioned above were repeated, but this time adjusting for assigned dose level of NaPBA or HPN-100 at the time of the blood draw. Since the UCD population consisted of a mixture of children and adults undergoing both short-term therapy and long-term therapy, total assigned daily dose for UCD patients was standardized to body surface area and reported in PBA-equivalent grams meter$^2$. Healthy and HE subjects were all adults and their assigned dose was not adjusted by body surface area. Dose levels for healthy and HE subjects were reported in HPN-100 equivalent mL. Dose levels for UCD subjects were reported in NaPBA-equivalent grams.

The excess of PAA over PAGN, indicated by larger ratios as PAA increases, was evident across all dosage groups, disease populations, and types of treatment in UCD patients (i.e., applies to both NaPBA and HPN-100). This finding suggests that analysis of the precursor (PAA) to product (PAGN) ratio may be predictive of the efficiency of conversion among patients with or without liver dysfunction (UCD patients have normal liver function apart from their urea cycle dysfunction) and independently of dose. As a corollary, the presence of liver dysfunction (e.g. cirrhosis) by itself, is not necessarily a reliable determinant of whether a particular patient is at risk for high PAA levels.

The ability of PAA:PAGN ratios to predict extremely high plasma PAA concentrations was determined by modeling the probability that a subject would exceed a PAA value of 400 or 500 µg/mL anytime during a 24 hour dosing period, based on the ratio of PAA to PAGN computed at pre-dose (presumably trough), 12 hours after dosing (presumably peak), and the maximum ratio encountered anytime between pre-dose and 12 hours post-dose. This interval of 0-12 hours was chosen for practical reasons, as it would encompass the entire interval corresponding to the usual outpatient visit.

Since subjects could have multiple dosing periods within a given clinical study, the probability was modeled using Generalized Estimating Equations. Three categorizations of ratios were modeled: a.) [0- <=2.0] [>2.0], b.) [0-<= 2.5, >2.5], c.) [0-<= 3.0, > 3.0]. The models were repeated with PAA values greater than or equal to 500 µg/mL considered extreme. Results are summarized in Table 3.

TABLE 3

Probabilities of extreme PAA values encountered during 24 hour PK sampling with PAA:PAGN ratios (all subjects combined)

| PAA Value Considered High | | Time of Blood Draw Used For Ratio Classification | Observed Ratio of PAA/PAGN | Probability that a Subject With This Ratio Will Exceed High Value* (%) | Bootstrapped 95% Confidence Interval** |
|---|---|---|---|---|---|
| [<=2.0, >2.0] | >=400 µg/mL | t = 0 (fasting) | <=2.0 | 0.005 (0.5%) | 0.004, 0.020 |
| | | | >2.0 | 0.164 (16.4%) | 0.041, 0.281 |
| | | t = 12 hours | <=2.0 | 0.003 (0.3%) | 0.004, 0.021 |
| | | | >2.0 | 0.227 (22.7%) | 0.048, 0.412 |
| | | MAX (0-12) | <=2.0 | 0.002 (0.2%) | 0.004, 0.010 |
| | | | >2.0 | 0.143 (14.3%) | 0.036, 0.263 |

TABLE 3-continued

Probabilities of extreme PAA values encountered during 24 hour
PK sampling with PAA:PAGN ratios (all subjects combined)

| PAA Value Considered High | | Time of Blood Draw Used For Ratio Classification | Observed Ratio of PAA/PAGN | Probability that a Subject With This Ratio Will Exceed High Value* (%) | Bootstrapped 95% Confidence Interval** |
|---|---|---|---|---|---|
| | >=500 μg/mL | t = 0 (fasting) | <=2.0 >2.0 | did not converge | |
| | | t = 12 hours | <=2.0 >2.0 | did not converge | |
| | | MAX (0-12) | <=2.0 >2.0 | did not converge | |
| [<=2.5, >2.5] | >=400 μg/mL | t = 0 (fasting) | <=2.5 >2.5 | 0.008 (0.8%) 0.191 (19.1%) | 0.004, 0.023 0.053, 0.366 |
| | | t = 12 hours | <=2.5 >2.5 | 0.007 (0.7%) 0.364 (36.4%) | 0.004, 0.016 0.125, 0.752 |
| | | MAX (0-12) | <=2.5 >2.5 | 0.003 (0.3%) 0.200 (20.0%) | 0.004, 0.013 0.050, 0.381 |
| | >=500 μg/mL | t = 0 (fasting) | <=2.5 >2.5 | 0.003 (0.3%) 0.084 (8.4%) | 0.004, 0.011 0.029, 0.214 |
| | | t = 12 hours | <=2.5 >2.5 | did not converge | |
| | | MAX (0-12) | <=2.5 >2.5 | did not converge | |
| [<=3, >3] | >=400 μg/mL | t = 0 (fasting) | <=3.0 >3.0 | 0.010 (1.0%) 0.205 (20.5%) | 0.004, 0.025 0.059, 0.398 |
| | | t = 12 hours | <=3.0 >3.0 | 0.013 (1.3%) 0.250 (25.0%) | 0.004, 0.028 0.113, 0.576 |
| | | MAX (0-12) | <=3.0 >3.0 | 0.003 (0.3%) 0.229 (22.9%) | 0.004, 0.014 0.059, 0.438 |
| | >=500 μg/mL | t = 0 (fasting) | <=3.0 >3.0 | 0.003 (0.3%) 0.102 (10.2%) | 0.004, 0.010 0.032, 0.255 |
| | | t = 12 hours | <=3.0 >3.0 | did not converge | |
| | | MAX (0-12) | <=3.0 >3.0 | did not converge | |

Analysis repeated for each ratio cut off category independently.
*Probability derived from Generalized Estimating Equations model with logit link function.
**Confidence interval derived from method disclosed in Davison & Hinkley, "Bootstrap Methods and Their Application," Cambridge Univ. Press (1997), pp. 358-362, using 1000 re-samplings of original data.

Because of the sparseness of samples in which PAA equaled or exceeded 500 μg/mL, 400 μg/mL proved to be a more stable and predictable target (i.e. high) value. Of the three categorizations of ratio considered, the cutpoint of 2.5 was the best discriminator and predictor of the risk of experiencing an high value. For example, referring to Table 3, a subject with a PAA:PAGN ratio>2.5 at t=12 hours after dosing has a 36.4% chance (95% c. i.=0.125, 0.752) of exceeding 400 μg/mL in PAA sometime during the 24-hour PK sampling period.

Results were similar whether the ratio was computed from plasma drawn at pre-dose, 12 hours after initiation of dosing, or the maximum ratio encountered anytime between pre-dose and 12 hours after initiation of dosing.

Due to the very high intra-day variability of plasma PAA levels, a PAA:PAGN ratio observed as exceeding 2.0 at a certain time following dosing may not remain greater than 2.0 in subsequent times. To evaluate the optimal time for obtaining a PAA:PAGN ratio measurement (i.e., the time that gives the greatest probability of correctly detecting a subject whose PAA:PAGN ratio ever equals or exceeds 2.0 during the dosing period), ratios were evaluated at 0 (pre-dose) and 2, 4, 6, 8, 10, and 12 hours post-dosing and modeled using GEE methodology. Pairwise differences in sensitivity between time points were evaluated using LS means and confidence intervals were computed.

Figure 3:
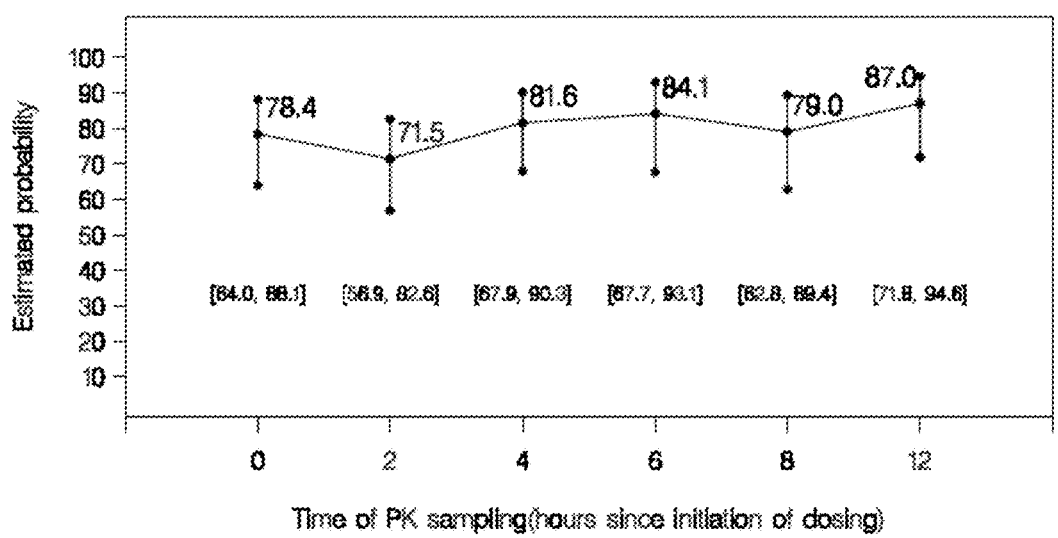
FIG. 3: Estimated probability (95% confidence interval (c.i.)) of correctly detecting elevated plasma PAA:PAGN ratio (≥2.0) with a single blood sample at a designated time.

FIG. 3 plots the estimated probabilities of correctly detecting a ratio profile that ever equals of exceeds 2.0. With the exception of time=2 hours and time=10 hours, time points of 0, 4, 6, 8, and 12 hours post-dosing were equally effective in detecting subjects who equal or exceed a PAA:PAGN ratio of 2.0 at some point during the dosing period. Sensitivities were in the range of 75-90 percent. There were too few blood samples collected at t=10 hours to analyze inter-time differences. Differences in predictive value were observed. For example, blood samples collected at t=2 hours post-dosing had a significantly lower probability of detecting subjects who equal or exceed a PAA:PAGN ratio of 2.0 than samples collected at t=0 (p=0.036), 4 (p=0.032), or 6 hours (p=0.017) post-dosing (p values are comparisons of t=2 hour probability with other time points). Similarly, a sample collected at t=12 hours following initiation of dosing had the highest probability (87%) of detecting a subject whose ratio ever equals or exceeds 2.0. However, for practical clinical purposes, the differences in predictive value among time points was trivial relative to the dramatically greater variability in PAA values themselves, meaning that random blood draws can be used for measurement of PAA:PAGN ratio.

Further exploration of the fluctuation of PAA:PAGN ratios over time was conducted by dividing the subject population into cohorts according to the maximum PAA:PAGN ratio achieved during the 24-hour PK sampling time during the dosing period. Cohorts were divided into "low" (maximum ratio<=2.0), "medium" (maximum ratio: 2.01-2.50), and "high" (maximum ratio>2.50). Each cohort was then followed over time during the dosing period at t=0 hours (pre-dose), 4, 6, and 8 hours post-dosing and the distribution of PAA:PAGN ratios within the cohort summarized using a box-and-whisker plot at each time point. This analysis was conducted for the PK-timepoint-specific population as a whole (analysis population B) as well as for each disease subpopulation separately.

Figure 4:
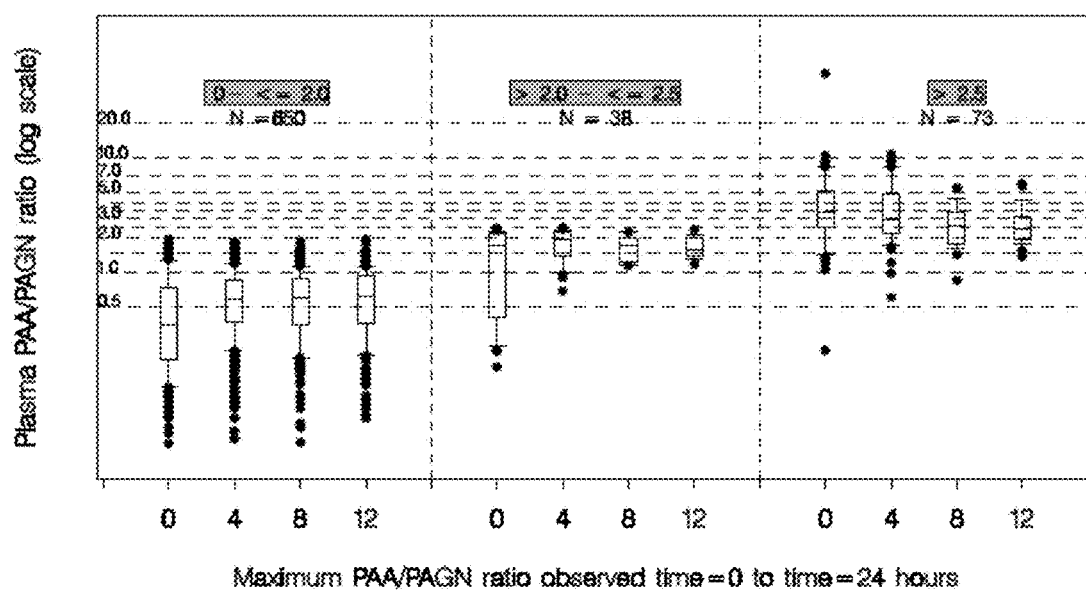
FIG. 4: Distribution of plasma PAA:PAGN ratio (log scale) by time since dosing (hours) and category of maximum PAA:PAGN ratio in all subjects combined.

FIG. 4 plots the progression of ratios for all subjects combined. Each "panel" of the plot that divides the graphing space into thirds represents one cohort. Subjects in the high cohort had high ratios throughout the day and not only at a particular time point. Therefore, subjects in this cohort (n=73 subject/dosing periods) started with high ratios (median ratio>2.5) and remained high throughout the first 12 hours. This finding is consistent with the findings plotted in FIG. 3 which revealed the consistency of sensitivity in ratios.

The relationship between PAA levels and PAA:PAGN ratios was further analyzed by categorizing ratios into "low" (maximum ratio<=2.0), "medium" (maximum ratio: 2.01-2.50), and "high" (maximum ratio>2.50). Unlike the previous analysis, this analysis did not associate subject/dosing periods with particular cohorts (i.e., all samples and all time points are combined with regard to the subject or dosing period).

Figure 5A:
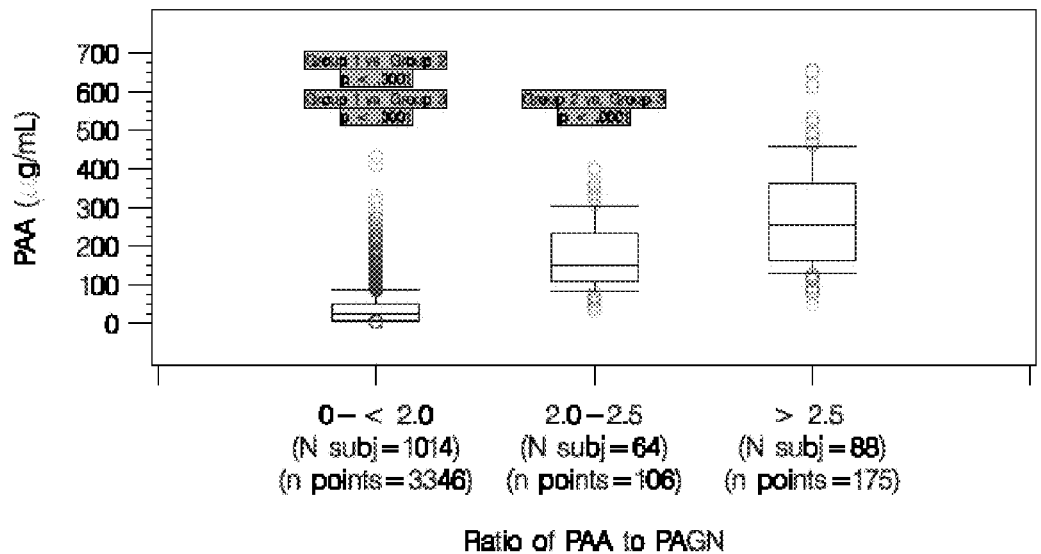
FIG. 5: Distribution of plasma PAA concentrations (μg/mL) by PAA:PAGN ratio for (A) all subjects and (B) UCD and HE subjects.
Figure 5B:
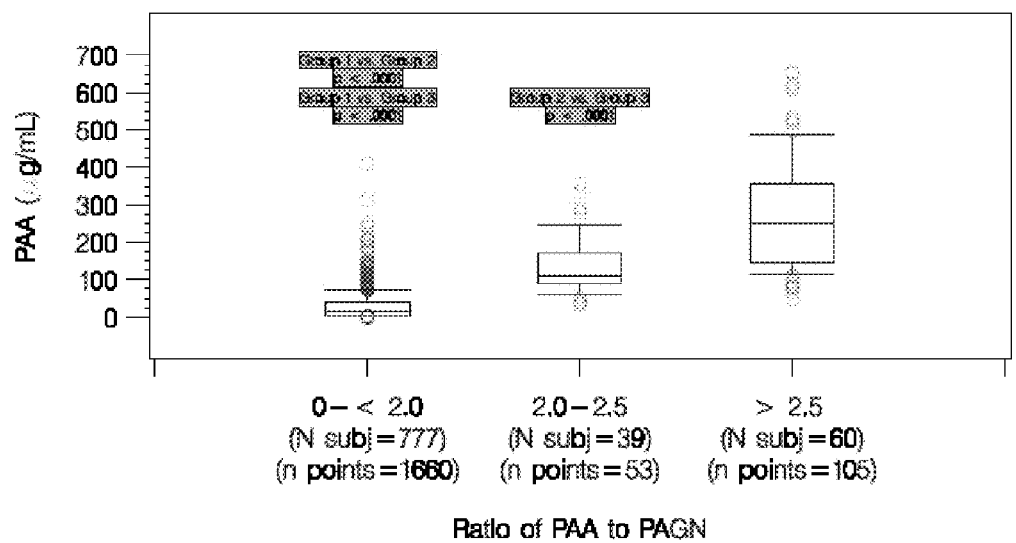

FIG. 5A shows the box-and-whisker plots of PAA levels grouped by the above categories of PAA:PAGN ratio for all subjects, while FIG. 5B shows the same for UCD and HE subjects only. The results were very similar in both analysis sets. Following a statistically significant overall Kruskal-Wallis test (p<0.0001), pairwise comparisons of PAA levels were conducted using Wilcoxon-Mann-Whitney with a Bonferroni alpha correction of (0.0167). In both analysis sets, ratios greater than 2.5 had significantly higher PAA levels (p<0.001) than either ratios between 2.0-2.5 or ratios less than 2.0. Furthermore, ratios between 2.0-2.5 were associated with significantly higher PAA levels than ratios less than 2.0 (p<0.001).

Example 2

Analysis of PAA:PAGN Ratio as a Guide to Dose Adjustment and Monitoring in a UCD Patient Patient 1 was a 15 year old partial OTC female receiving HPN-100 as maintenance therapy for her UCD at a dose of 9 mL/day. The patient's ammonia had been controlled since her last routine visit around 6 months ago, but she was complaining of headache and lack of appetite for the past 3 days. Ammonia and metabolite levels were tested after overnight fasting and showed the following results: ammonia 55 µmol/L, PAA and PAGN below levels of quantification. The physician suspected non-compliance with drug and repeated the tests in midday several hours after lunch and found the following results: ammonia: 117 µmol/L; PAA 55 µg/L, PAGN 121 µg/L, and PAA:PAGN ratio approximately 0.5. The patient indicated that she had been fully compliant with her medication. Based on the PAA to PAGN ratio of 0.5 and ammonia of 117, the physician decided to increase the dosage of HPN-100 to 12 mL/day. After one week of treatment with the new dose of HPN-100, all symptoms resolved and the laboratory tests after overnight fasting showed the following: ammonia 9 µmol/L; PAA 12.9 µg/L, PAGN of 9 µg/L, and PAA:PAGN ratio of 1.3. Midday tests showed the following: ammonia 35 µmol/L, PAA 165 µg/L, PAGN 130 µg/L, and PAA:PAGN ratio of ~1.2. The patient was considered controlled and the dose remained at 12 mL/day.

Example 3

Analysis of PAA:PAGN Ratio as a Guide to Dose Adjustment in a UCD Patient

Patient 2 was a 1 year old male OTC receiving 600 mg/kg of NaPBA per day. The patient presented with poor feeding and somnolence. Laboratory tests showed ammonia levels of <9 µmol/L, PAA levels of 530 µg/L, PAGN levels of 178 µg/L, and a PAA:PAGN ratio of >2.5, suggesting that the dose of NaPBA was greater than the patient could effectively convert to PAGN. The treating physician decided to decrease the dose of NaPBA to 450 mg/Kg/day. After one week of treatment with the new dosage, the patient's mother reported that he was eating well and was no longer somnolent. Laboratory tests showed the following: ammonia 20 µmol/L, PAA 280 µg/L, and PAGN 150 µg/L.

Example 4

Analysis of PAA:PAGN Ratio as a Guide to Assessment of Importance of a High PAA Level in a UCD Patient Patient 3 is a 25 year old OTC female who is being treated with HPN-100. The physician had to increase the dose of HPN-100 several times in order to achieve clinical and blood ammonia within normal limits. Patient 3 was treated at a dose of 18 mL/day for her UCD for the past month. In her next office visit, she did not have any complaints and the following lab results were reported: ammonia 22 µmol/L, PAA 409 µg/L, PAGN 259 µg/L, and PAA:PAGN ratio of 1.5. Despite the patient's relatively high PAA levels, the PAA:PAGN ratio indicated that the subject was being adequately treated and that the patient was able to effectively metabolize the high dose of HPN-100 that she was receiving. The physician decided to continue the treatment as planned.

Example 5

Analysis of PAA:PAGN Ratio as a Guide to Dose Adjustment in a Patient with Spinal Muscular Atrophy and Concomitant Liver Disease Patient 4 was a 2 year old female being treated with a liquid form of NaPBA for her type II SMA. The patient also suffered from chronic hepatitis C virus infection acquired perinatally from her infected mother. The patient had been having mild to moderate elevation of transaminases since birth, with episodes of icterus and a recent liver biopsy has confirmed presence of chronic hepatitis and cirrhosis. The patient was receiving 4 g of NaPBA per day, and the physician wanted to increase the dosage due to the patient's growth but was concerned about the effects of liver dysfunction on drug metabolism. The physician ordered plasma PAA and PAGN levels and the results were as follows: PAA 110 µg/L, PAGN 85 µg/L, PAA:PAGN ratio of 1.2. The physician decided to increase the dosage of NaPBA to 6 g/day, and repeated the plasma metabolite level measurements after one week of treatment with the new regimen. The results were as follows: PAA 155 µg/L, PAGN 110 µg/L, and PAA:PAGN ratio of 1.4. The physician decided to leave the patient on 6 g/day of NaPBA since his liver seems to have adequate capacity to metabolize 6 g of NaPBA.

Example 6

Analysis of PAA:PAGN Ratio as a Guide to Dose Adjustment in a Patient with Huntington's Disease and Concomitant Liver Disease Patient 5 was a 56 year old male diagnosed with Huntington's disease several years ago. He also had a history of alcohol abuse and was diagnosed with alcoholic cirrhosis last year. His wife enrolled him in clinical trials that involved an experimental drug delivering PBA at a slow rate, thereby enabling once-a-day dosing of the drug. The study had an option for dose escalation after 2 weeks of treatment if clinically safe. Although the protocol did not exclude patients with liver dysfunction, the investigator was concerned about PBA metabolism and possible accumulation of PAA in higher doses due to the patient's liver dysfunction. The investigator enrolled the patient in the low dose group and performed plasma PBA, PAA and PAGN measurements after 6 weeks of treatment with experimental drug. The patient reported improvement in his HD symptoms with no specific complains. Plasma metabolite levels after six weeks of treatment were as follows: PBA 45 µg/L; PAA 159 µg/L, and PAGN 134 µg/L. The dosage of the drug was increased by 50%. After four days of treatment at the new dosage, the patient started to complain about short episodes of somnolence. The investigator performed a blood test and observed the following: PBA 44 µg/L; PAA 550 µg/L, PAGN 180 µg/L, and PAA:PAGN ratio of >3. The PAA:PAGN ratio of greater than 2.5 indicated that the patient's liver could not effectively metabolize the higher dose of the drug, and the investigator therefore decided to reduce the dosage of the experimental drug and not continue dose escalation.

Example 7

Analysis of PAA:PAGN Ratio as a Guide to Dose Adjustment in a Patient with MSUD

Patient 6 was a 4 year old female being treated with HPN-100 for MSUD. The patient was receiving 6 mL of HPN-100 once a day, and the physician wanted to increase the dosage due to the patient's growth. Midday plasma PAA and PAGN measurements after the dose of medication were as follows: PAA 550 µg/L, PAGN 180 µg/L, and PAA:PAGN ratio of >2.5. The physician believed a lower dosage of HPN-100 would not be as effective for the patient, and decided to change the dosing regimen to 3 mL BID instead of 6 mL QD based on the high PAA:PAGN ratio. The tests were repeated after one week of treatment with the new BID regimen, with the following results: PAA 350 µg/L, PAGN 190 µg/L, and PAA:PAGN ratio of 1.8. Based on the ratio of 1.8, the physician decided to leave the patient on 3 mL BID since she can efficiently use a total dose of 6 mL/day given in divided doses but not as a bolus.

Example 8

Analysis of PAA:PAGN Ratio as a Guide to Monitor a Patient with HE and Hepatic Impairment Patient 7 was a 55 year old Caucasian male diagnosed with alcoholic cirrhosis 3 years ago. His transaminase levels had been mildly elevated and he had recently experienced mild episodes of HE. In the last assessment at the time of hospital admission for a grade 2 HE episode, the patient had a blood ammonia of 85 µmol/L, ALT of 55 U/L, and AST of 47 U/L, and a calculated MELD score of 11. The physician decided to start an ammonia scavenging therapy for the patient and treated him with HPN-100 6 mL BID. The patient returned for a follow up visit after 3 months, during which time he had experienced no episodes of HE. His laboratory assessments showed the following: ammonia of 30 µmol/L, plasma PAA level of 285 µg/mL, PAGN level of 120 µg/L, ALT of 66 U/L, AST of 50 U/L, and calculated MELD score of 13. The physician suspected that the patient's hepatic function may be deteriorating and was concerned about possible accumulation of PAA. She calculated the ratio of PAA to PAGN as 2.4, and confirmed that the patient had not experienced any unusual symptoms such as dizziness, headache, or nausea. Considering patient's ammonia control, lack of specific side effects, and clinical remission, the physician decided not to change the dose and to see the patient in two weeks to repeat the laboratory tests. The physician also warned the patient to call her immediately if he experienced any of these symptoms. In two weeks, the patient's laboratory assessments were essentially unchanged from the previous visit, with a PAA to PAGN ratio of 2.3, and the patient did not report any unusual symptoms. Based on the PAA:PAGN ratio of less than 2.5, the physician decided to continue dosing with 6 mL BID of HPN-100 until the next routine visit.

Example 9

Analysis of PAA:PAGN Ratio as a Guide to Monitoring Treatment in a Patient with Parkinson's Disease HPN-100 treatment was initiated at a dose of 4 mL twice a day in a patient with Parkinson's Disease to produce target circulating levels of PAA expected to produce clinical benefit. After one week of treatment, the patient's circulating PAA level of 50 µg/mL was below the target range, and the PAA:PAGN ratio was determined to be 0.9. The physician concluded that the HPN-100 dose could be safely adjusted upward, and the dose was increased by 50% to 6 mL BID. The PAA level and PAA/PAGN ratio one week later were found to be 75 µg/mL and 1.4, respectively. Since 75 µg/mL was still below the therapeutic PAA target level and the PAA:PAGN ratio of 1.4 indicated that conversion of PAA to PAGN had not been saturated, the patient's dosage was increased again by 50% to 9 mL BID. One week later, the patient's PAA and PAA:PAGN ratio were found to be 159 µg/mL and 2.6, respectively. Since the target PAA level was now approximately therapeutic but the PAA:PAGN ratio indicated that PAA to PAGN conversion was approaching saturation, HPN-100 dosage was decreased to 8 mL BID, at which time the patient's circulating PAA level was determined to be close to the target range and his PAA:PAGN ratio was determined to be 2. The patient's dose was not further adjusted and he continued to be monitored.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Brahe Eur J Hum Genet 13:256 (2005)
2. Bruneti-Pieri Human Molec Genet 20:631 (2011)
3. Brusilow Science 207:659 (1980)
4. Brusilow Pediatr Res 29:147 (1991)
5. Brusilow Metabolism 42:1336 (1993)
6. Chung Clin Cancer Res 6:1452 (2000)
7. Cudkowicz ALS 10:99 (2009)
8. Hines Pediatr Blood Cancer 50:357 (2008)
9. Hogarth Mov Disord 22:1962 (2007)
10. Lee Mol Genet Metab 100:221 (2010)
11. Lichter Mol Genet Metab 103:323 (2011)
12. McGuire Hepatology 51:2077 (2010)
13. Mercuri Neuromuscul Disord 14:130 (2004)
14. Mokhtarani Mol Genet Metab 105:342 (2012)
15. Moldave J Biol Chem 229:463 (1957)
16. Monteleone Mol Genet Metab 105:343 (2012)
17. Ong Am J Med 114:188 (2003)
18. Perrine Pediatr Ann 37:339 (2008)
19. Ryu J Neurochem 93:1087 (2005)
20. Thiebault Cancer Res 54:1690 (1994)
21. Thiebault Cancer 75:2932 (1995)

What is claimed is:

1. A method of treating a urea cycle disorder in a subject comprising administering to a subject having a plasma PAA to PAGN ratio outside the target range of 1 to 2, a dosage of glyceryl tri-[4-phenylbutyrate] (HPN-100) effective to achieve a plasma PAA to PAGN ratio within the target range of 1 to 2.

2. A method of treating a urea cycle disorder in a subject comprising administering to a subject having a plasma PAA to PAGN ratio outside the target range of 1 to 2.5, a dosage of glyceryl tri-[4-phenylbutyrate] (HPN-100) effective to achieve a plasma PAA to PAGN ratio within the target range of 1 to 2.5.

* * * * *